United States Patent [19]

Kim

[11] Patent Number: 4,683,301

[45] Date of Patent: Jul. 28, 1987

[54] CARBAPENEM ANTIBIOTICS

[75] Inventor: Choung U. Kim, Manlius, N.Y.

[73] Assignee: Bristol-Myers Company, New York, N.Y.

[21] Appl. No.: 656,838

[22] Filed: Oct. 2, 1984

Related U.S. Application Data

[63] Continuation-in-part of Ser. No. 366,627, Apr. 8, 1982, abandoned.

[51] Int. Cl.$^4$ .................... C07D 487/04; A61K 31/40
[52] U.S. Cl. ..................................... 540/350; 540/310; 514/210
[58] Field of Search ................ 260/245.2 R; 540/350, 540/310; 514/210

[56] References Cited

U.S. PATENT DOCUMENTS

| | | | |
|---|---|---|---|
| 3,950,357 | 4/1976 | Kahan et al. | 260/245.2 T |
| 4,218,463 | 8/1980 | Christensen et al. | 424/274 |
| 4,232,036 | 11/1980 | Christensen et al. | 424/274 |
| 4,235,920 | 11/1980 | Christensen et al. | 260/245.2 T |
| 4,309,346 | 1/1982 | Christensen et al. | 260/239 |
| 4,318,912 | 3/1982 | Christensen et al. | 424/262 |
| 4,350,631 | 9/1982 | Christensen et al. | 260/245.2 T |
| 4,378,315 | 3/1983 | Christensen et al. | 260/239 |
| 4,536,335 | 8/1985 | Kim et al. | 260/245.2 R |

FOREIGN PATENT DOCUMENTS

| | | |
|---|---|---|
| 0017992 | 10/1980 | European Pat. Off. |
| 0037082 | 3/1981 | European Pat. Off. |
| 0024832 | 3/1981 | European Pat. Off. |
| 0021082 | 7/1981 | European Pat. Off. |
| 0037080 | 10/1981 | European Pat. Off. |
| 0037081 | 10/1981 | European Pat. Off. |
| 0040408 | 11/1981 | European Pat. Off. |
| 0038869 | 11/1981 | European Pat. Off. |
| 0054917 | 12/1981 | European Pat. Off. |
| 0074599 | 3/1983 | European Pat. Off. |
| 0090366 | 10/1983 | European Pat. Off. |
| 0010317 | 12/1983 | European Pat. Off. |
| 0001628 | 1/1984 | European Pat. Off. |
| 0007973 | 2/1984 | European Pat. Off. |
| 0001627 | 4/1984 | European Pat. Off. |

OTHER PUBLICATIONS

Recent Advances in the Chemistry of β-Lactam Antibiotics, The Royal Society of Chemistry, London, 1981, pp. 240-254.

Primary Examiner—Nicholas S. Rizzo
Attorney, Agent, or Firm—David M. Morse

[57] ABSTRACT

Disclosed are novel carbapenem derivatives characterized by a 2-substituent of the formula

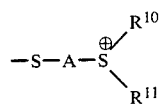

wherein A represents $C_2$-$C_6$ straight or branched chain alkylene group and $R^{10}$ and $R^{11}$ each independently represents optionally substituted aliphatic, cycloaliphatic, cycloaliphatic-aliphatic, aryl, heterocyclyl, heterocyclyl-aliphatic, heteroaryl or heteroaraliphatic, or $R^{10}$ and $R^{11}$ taken together with the $S^{\oplus}$ to which they are attached represent an optionally substituted sulfur-containing heterocyclic ring. Such derivatives are useful as potent antibacterial agents. Also disclosed are processes for the preparation of such derivatives.

8 Claims, No Drawings

CARBAPENEM ANTIBIOTICS

CROSS-REFERENCE TO RELATED APPLICATION

This application is a continuation-in-part application of co-pending application Ser. No. 366,627 filed Apr. 8, 1982, abandoned.

BACKGROUND OF THE INVENTION

1. Field of the Invention

The present invention is directed to new carbapenem antibiotics in which the 2-substituent has the formula $$-S-A-\overset{\oplus}{S}\overset{R^{10}}{\underset{R^{11}}{\diagdown}}$$

wherein A is $C_2$–$C_6$ straight or branched chain alkylene and $R^{10}$ and $R^{11}$ each independently represent optionally substituted aliphatic, cycloaliphatic, cycloaliphatic-aliphatic, aryl, heterocyclyl, heterocyclyl-aliphatic, heteroaryl or heteroar-aliphatic radicals, or $R^{10}$ and $R^{11}$ when taking together with the $$S^{\oplus}$$

to which they are attached represent an optionally substituted sulfur-containing heterocyclic ring.

2. Description of the Prior Art

A number of β-lactam derivatives containing the carbapenem nucleus have been disclosed in the literature. These carbapenem derivatives have been reported to possess utility as antibacterial agents and/or β-lactamase inhibitors.

The initial carbapenem compounds were natural products such as thienamycin of the formula obtained by fermentation of *Streptomyces cattleya* (U.S. Pat. No. 3,950,357). Thienamycin is an exceptionally potent broad-spectrum antibiotic which possesses notable activity against various Pseudomonas species, organisms which have been notoriously resistant to β-lactam antibiotics.

Carbapenems of the general formula wherein $R^1$ is H or acyl and $R^8$ is H or substituted or unsubstituted: alkyl, alkenyl, alkynyl, cycloalkyl, cycloalkylalkyl, alkylcycloalkyl, aryl, aralkyl, aralkenyl, aralkynyl, heteroaryl, heteroaralkyl, heterocyclyl or heterocyclylalkyl, are disclosed in U.S. Pat. No. 4,218,463. There is no disclosure of any $R^8$ substituents of the type $$-A-\overset{\oplus}{S}\diagup$$

in which A is alkylene.

Compounds of the formula wherein $R^5$, $R^6$ and $R^7$ are independently selected from H and substituted or unsubstituted: alkyl, alkenyl, alkynyl, cycloalkyl, cycloalkenyl, cycloalkenylalkyl, cycloalkylalkyl, aryl, aralkyl, heteroaryl or heteroaralkyl are disclosed in U.S. Pat. No. 4,235,920. Among the compounds disclosed in U.S. Pat. No. 4,235,920 is wherein A is a pharmaceutical acceptable anion. The above-mentioned quaternary amine derivative is also described in *Recent Advances in Chemistry of β-Lactam Antibiotics,* Royal Society of Chemistry, London, 1981, pg 240–254, where its antibacterial activity on average is reported as approximately ½ to ⅔ that of thienamycin.

Compounds of the formula wherein attached to the amino nitrogen group of thienamycin represents a mono- or polycyclic N-containing heterocyclic group and R is H, substituted or unsubstituted: alkyl, aryl, alkenyl, heterocyclyalkenyl, aralkenyl, heterocyclyalkyl, aralkyl, —NR₂, COOR, CONR₂, —OR, or CN, are disclosed in European Patent Application 21082.

European Patent Application No. 40,408 discloses compounds of the formula

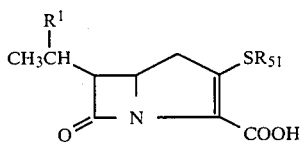

wherein $R^1$ is H, methyl or hydroxyl and $R_{51}$ is a monovalent organic group including inter alia heterocyclicalkyl.

European Patent Application No. 38,869 discloses compounds of the formula

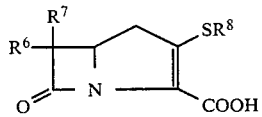

wherein $R^6$, $R^7$, and $R^8$ are independently selected from the group consisting of hydrogen, substituted and unsubstituted: alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; aryl, such as phenyl; aralkyl, aralkenyl, and aralkynyl wherein the aryl moiety is phenyl and the aliphatic portion has 1–6 carbon atoms; heteroaryl, heteroaralkyl, heterocyclyl and heterocyclylalkyl; wherein the substituent or substituents relative to the above-named radicals are selected from the group consisting of:

—$X^o$ halo (chloro, bromo, fluoro)
—OH hydroxy
—$OR^1$ alkoxy, aryloxy $$-O\overset{O}{\underset{\|}{C}}NR^1R^2 \text{ carbamoyloxy}$$

$$-\overset{O}{\underset{\|}{C}}NR^1R^2 \text{ carbamoyl}$$

—$NR^1R^2$ amino $$-\!\!\!\!\underset{NR^1R^2}{\overset{NR^1}{\diagup\!\!\!\diagdown}} \text{ amidino}$$

—$R^1$
—$NO_2$ nitro

—$\overset{\oplus}{N}(R^1)_3$ tri-substituted amino ($R^1$ group independently chosen)

—$\underset{|}{\overset{R^1}{C}}=NOR^2$ oximino

—$SR^1$ alkyl- and arylthio
—$SO_2NR^1R^2$ sulfonamido $$-NH\overset{O}{\underset{\|}{C}}NR^1R^2 \text{ ureido}$$

$$R^1\overset{O}{\underset{\|}{C}}NR^2- \text{ amido}$$

—$CO_2H$ carboxy

—$CO_2R^1$ carboxylate $$-\overset{O}{\underset{\|}{C}}R^1 \text{ acyl}$$

$$-O\overset{O}{\underset{\|}{C}}R^1 \text{ acyloxy}$$

—SH mercapto $$-\overset{O}{\underset{\|}{S}}R^1 \text{ alkyl and aryl sulfinyl}$$

$$-\overset{O}{\underset{\underset{O}{\|}}{\overset{\|}{S}}}R^1 \text{ alkyl and aryl sulfonyl}$$

—CN cyano
—$N_3$ azido wherein, relative to the above listed substituents on $R^6$, $R^7$, and $R^8$, the groups $R^1$ and $R^2$ are independently selected from: hydrogen, alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; aryl, such as phenyl; aralkyl, aralkenyl, and aralkynyl wherein the aryl moiety is phenyl and the aliphatic portion has 1–6 carbon atoms; heteroaryl, heteroaralkyl, heterocyclyl and heterocyclylalkyl and wherein the hetero atom or atoms in the above-named heterocyclic moieties are selected from the group consisting of 1–4 oxygen, nitrogen or sulphur atoms and wherein the alkyl moieties associated with said heterocyclic moieties have 1–6 carbon atoms. (See also European Patent Application Nos. 1627, 1628, 10317, 17992, 37080, 37081 and 37082).

European Patent Application No. 24832 discloses compounds of the formula

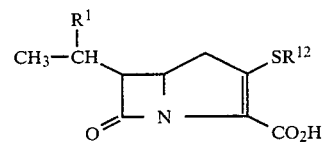

wherein $R^1$ is H or a group selected from OH, $OSO_3H$ or a salt or $C_{1-4}$ alkyl ester thereof, $OR^2$, $SR^3$, $OCOR^2$, $OCO_2R^3$ or $OCONHR^3$, where $R^2$ is a $C_{1-6}$ alkyl group or an optionally substituted benzyl group and $R^3$ is a $C_{1-6}$ alkyl group or an optionally substituted benzyl or phenyl group and $R^{12}$ is $C_{1-6}$ alkyl, $C_{2-6}$ alkenyl, $C_{3-6}$ alkynyl wherein the triple bond is not present on the carbon adjacent to the sulfur atom, aralkyl, $C_{1-6}$ alkanoyl, aralkanoyl, aryloxyalkanoyl or arylcarbonyl, any of such $R^{12}$ groups being optionally substituted, as antibacterial agents.

European Patent Application No. 38,869 mentioned above discloses synthesis of the carbapenem derivatives via intermediates of the general formula

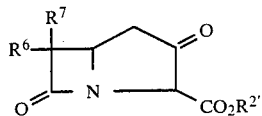

wherein $R^6$ and $R^7$ are as defined above and $R^{2'}$ is a readily removable carboxyl protecting group. Also disclosed as intermediates are the compounds of the formula

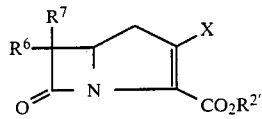

wherein X is described as a leaving group.

European Patent Application No. 7973 discloses the intermediates of the formula

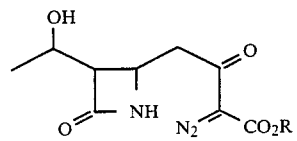

and

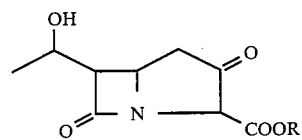

where R is hydrogen or an ester group. The diazo intermediate is also disclosed in U.S. Pat. No. 4,378,315 while the keto intermediate is disclosed in U.S. Pat. No. 4,318,912.

At the Gordon Research Conference on Medicinal Chemistry held at New London, N.H. on Aug. 2-6, 1982, a handout was distributed in which a variety of carbapenem antibiotics were disclosed. Among the compounds disclosed on page 9 of the handout is the carbapenem of the formula

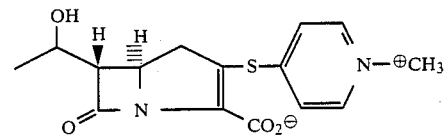

The above-mentioned carbapenem derivative is also disclosed on page 145 of European Patent Application 38869 and on page 252 of European Patent Application No. 17992.

U.S. Pat. No. 4,309,346 discloses carbapenem derivatives having 2-substituents of the formula

where $R^8$ may be inter alia heteroaralkyl in which the hetero atom or atoms in heteroaralkyl may be selected from the group consisting of 1-4 oxygen, nitrogen or sulfur atoms. No disclosure is made of any sulfonium groups such as are present in the compounds of the present invention.

European Patent Application No. 74,599 discloses 5,6-cis-carbapenem derivatives of the formula

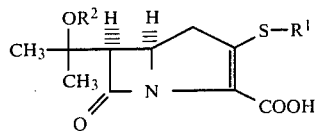

wherein $R^1$ is optionally substituted alkyl, cycloalkyl, cycloalkenyl, alkynyl, aryl, aralkyl or a 5 to 8 membered heterocyclic group containing 1 to 4 hetero atoms, and $R^2$ is hydrogen or a hydroxy-protecting group. There is no disclosure, however, of compounds where $R^1$ is

in which A is alkylene.

European Patent Application No. 90,366 discloses carbapenem antibiotics of the formula

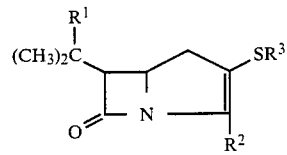

wherein $R^1$ is hydroxy, protected hydroxy or (lower)alkoxy, $R^2$ is carboxy or protected carboxy and $R^3$ is substituted aryl, optionally substituted pyridyl or an optionally substituted heterocyclic group containing 3-5 hetero atoms.

With respect to the 1-substituted carbapenems of the present invention, there is extensive literature disclosing carbapenems having a non-hydrogen 1-substituent and a 2-substituent similar to those disclosed in the above-mentioned references. Again, however, no art has been found teaching a 2-substituent of the type

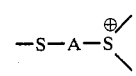

Examples of 1-substituted carbapenem references are indicated below.

European Patent Application No. 54,917 (equivalent to U.S. Pat. No. 4,350,631) discloses intermediates of the formula

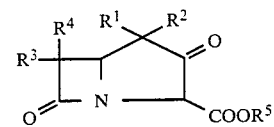

where $R^1$, $R^2$, $R^3$ and $R^4$ are independently selected from the group consisting of hydrogen ($R^1$ and $R^2$ are not both hydrogen), substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms; phenyl; aralkyl, aralkenyl, and aralkynyl wherein the aryl moiety is phenyl and the alkyl chain has 1-6 carbon atoms; heteroaryl, heteroaralkyl, heterocyclyl and heterocyclylalkyl wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, iodo, cyano and carboxy; and wherein the hetero atom or atoms in the above-named heterocyclic moieties are selected from the group consisting of 1-4 oxygen, nitrogen or sulfur atoms; and wherein the alkyl moieties of the above-recited substituents have 1-6 carbon atoms; $R^5$ is hydrogen, salt cation, a pharmaceutically acceptable ester moiety or a removable blocking group. Also disclosed are intermediates of the formula

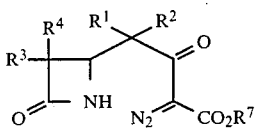

where $R^7$ is a carboxyl protecting group and $R^1$, $R^2$, $R^3$ and $R^4$ are as defined above.

European Patent Application No. 10,317 (see also U.S. Pat. No. 4,232,036) discloses carbapenem compounds of the general formula

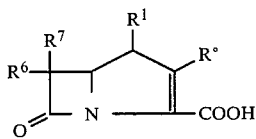

where R° is H or $-SR^8$; $R^1$, $R^6$, $R^7$ and $R^8$ are independently selected from the group consisting of hydrogen ($R^1$ is not H), substituted and unsubstituted: alkyl, alkenyl and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; phenyl; aralkyl, aralkenyl, and aralkynyl wherein the aryl moiety is phenyl and the alkyl chain has 1-6 carbon atoms; heteroaryl, heteroaralkyl, heterocyclyl and heterocyclylalkyl wherein the substituent or substituents relative to the above-named radicals are selected from the group consisting of: amino, mono-, di-, and trialkylamino, hydroxyl, alkoxyl, mercapto, alkylthio, phenylthio, sulfamoyl, amidino, guanidino, nitro, chloro, bromo, fluoro, cyano and carboxy; and wherein the hetero atom or atoms in the above-named heterocyclic moieties are selected from the group consisting of 1-4 oxygen, nitrogen or sulfur atoms; and wherein the alkyl moieties of the above-recited substituents have 1-6 carbon atoms.

Despite a vast number of literature references teaching preparation of carbapenem derivatives, including derivatives having 2-substituents of the type

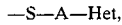
—S—A—Het, applicant believes he is the first to prepare carbapenem derivatives having a 2-substituent wherein the alkylene group A is attached directly to a sulfonium group, i.e. a group of the type

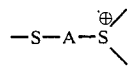

Although there are a vast number of carbapenem derivatives disclosed in the literature, there is still a need for new carbapenems since known derivatives may be improved upon in terms of spectrum of activity, potency, stability and/or toxic side effects.

SUMMARY OF THE INVENTION

The present invention provides a novel series of carbapenem derivatives characterized by a 2-substituent of the formula

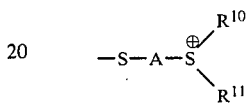

wherein A is $C_2$-$C_6$ straight or branched chain alkylene and $R^{10}$ and $R^{11}$ each independently represent optionally substituted aliphatic, cycloaliphatic, cycloaliphatic-aliphatic, aryl, heterocyclyl, heterocyclyl-aliphatic heteroaryl or heteroaraliphatic radicals, or $R^{10}$ and $R^{11}$ when taken together with the

$S^\oplus$ to which they are attached represent an optionally substituted sulfur-containing heterocyclic ring containing 0-2 double bonds and 0-2 additional heteroatoms selected from O, N and S, said ring being attached to A through a sulfur atom, thereby forming a sulfonium group. More specifically, the present invention provides carbapenem derivatives of the formula

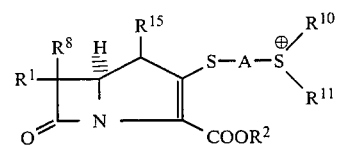

wherein $R^8$ is hydrogen and $R^1$ is selected from the group consisting of hydrogen; substituted and unsubstituted: alkyl, alkenyl and alkynyl, having from 1-10 carbon atoms; cycloalkyl and cycloalkylalkyl, having 3-6 carbon atoms in the cycloalkyl ring and 1-6 carbon atoms in the alkyl moieties; phenyl; aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hetero atom or atoms in the above-named heterocyclic moieties are selected from the group consisting of 1-4 oxygen, nitrogen or sulfur atoms and the alkyl moieties associated with said heterocyclic moieites have 1-6 carbon atoms; wherein the substituent or substituents relative to the above-named radicals are independently selected from the group consisting of $C_1$-$C_6$ alkyl optionally substituted by amino, halo, hydroxy or carboxyl halo

$-OR^3$

-continued

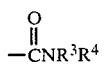

—NR³R⁴

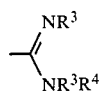

—SO₂NR³R⁴

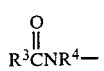

—CO₂R³
=O

—SR³

—CN
—N₃
—OSO₃R³
—OSO₂R³
—NR³SO₂R⁴

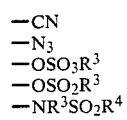

—NR³CO₂R⁴
—NO₂ wherein, relative to the above-named substituents, the groups R³ and R⁴ are independently selected from hydrogen; alkyl, alkenyl and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; phenyl; aralkyl, aralkenyl and aralkynyl wherein the aryl moiety is phenyl and the aliphatic portion has 1-6 carbon atoms; and heteroaryl, heteroaralkyl, heterocyclyl and heterocyclylalkyl wherein the hetero atom or atoms in the above-named heterocyclic moieties are selected from the group consisting of 1-4 oxygen, nitrogen or sulfur atoms and the alkyl moieties associated with said heterocyclic moieties have 1-6 carbon atoms, or R³ and R⁴ taken together with the nitrogen to which at least one is attached may form a 5- or 6-membered nitrogen-containing heterocyclic ring; R⁹ is as defined for R³ except that it may not be hydrogen; or wherein R¹ and R⁸ taken together represent $C_2$-$C_{10}$ alkylidene or $C_2$-$C_{10}$ alkylidene substituted by hydroxy; A is $C_2$-$C_6$ straight or branched chain alkylene; R² is hydrogen, an anionic charge or a conventional readily removable carboxyl protecting group, providing that when R² is hydrogen or a protecting group, there is also present a counter anion; R¹⁰ and R¹¹ each independently represents (a) $C_1$-$C_6$ alkyl, $C_2$-$C_6$ alkenyl, $C_2$-$C_6$ alkynyl, $C_3$-$C_6$ cycloalkyl or cycloalkylalkyl having 3-6 carbon atoms in the cycloalkyl ring and 1-6 carbon atoms in the alkyl moiety, said alkyl, alkenyl, alkynyl, cycloalkyl or cycloalkylalkyl group being optionally substituted by 1-3 substituents independently selected from hydroxy, $C_1$-$C_6$ alkoxy, $C_1$-$C_6$ alkanoyloxy, carboxy, $C_1$-$C_6$ alkoxycarbonyl, amono, $C_1$-$C_6$ alkylamino, di($C_1$-$C_6$)alkylamino, $C_1$-$C_6$ alkanoylamino, phenyl, phenyl substituted by 1-3 halo, $C_1$-$C_6$ alkoxy, $C_1$-$C_6$ alkyl, carboxy, carboxy ($C_1$-$C_6$)alkyl, amino, $C_1$-$C_6$ alkylamino, di($C_1$-$C_6$)alkylamino or di($C_1$-$C_6$)alkylamino($C_1$-$C_6$)alkyl, halo or oxo;

(b) phenyl optionally substituted by 1-4 halo, $C_1$-$C_6$ alkoxy, $C_1$-$C_6$ alkyl, carboxy, amino, $C_1$-$C_6$ alkylamino or di($C_1$-$C_6$)alkylamino groups;

(c) heterocyclyl or heterocyclylalkyl wherein the heterocyclic moiety is a 4-6 membered ring having 1-3 hetero atoms selected from O, N and S and the alkyl moiety has 1-6 carbon atoms, said heterocyclyl or heterocyclylalkyl ring being optionally substituted by 1-3 $C_1$-$C_6$ alkyl or $C_1$-$C_6$ alkoxy groups; or (d) heteroaryl or heteroaralkyl wherein the heterocyclic moiety is a 5-6 membered aromatic ring having 1-3 hetero atoms selected from O, N and S and the alkyl moiety has 1-6 carbon atoms, said heteroaryl or heteroaralkyl ring being optionally substituted by 1-3 $C_1$-$C_6$ alkyl, $C_1$-$C_6$ alkoxy, carboxy, carboxy($C_1$-$C_6$)alkyl, amino, $C_1$-$C_6$ alkylamino, di($C_1$-$C_6$)alkylamino, amino($C_1$-$C_6$)alkyl or di($C_1$-$C_6$)alkylamino($C_1$-$C_6$)alkyl groups; or wherein R¹⁰ and R¹¹ taken together with the

S⊕ to which they are attached represent a 4-6 member sulfur-containing heterocyclic ring containing 0-2 double bonds and 0-2 additional heteroatoms selected from O, N and S, said ring being attached to A through a sulfur atom, thereby forming a sulfonium group, said heterocyclic ring being optionally substituted by 1-3 substituents independently selected from:

$C_1$-$C_6$ alkyl optionally substituted by 1-3 hydroxy, $C_1$-$C_6$ alkoxy, carboxy, halo, amino, $C_1$-$C_6$ alkylamino or di($C_1$-$C_6$)alkylamino groups, hydroxy, $C_1$-$C_6$ alkoxy, $C_1$-$C_6$ alkanoyloxy, amino, $C_1$-$C_6$ alkylamino, di($C_1$-$C_6$)alkylamino, $C_1$-$C_6$ alkanoylamino, carboxy, $C_1$-$C_6$ alkoxycarbonyl, halo, oxo or phenyl; or wherein said heterocyclic ring

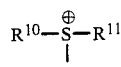

is fused to a $C_5$-$C_6$ carbocyclic ring, a phenyl ring, a 5-6 member heterocyclic ring or a 5-6 member heteroaryl ring, all of which rings may be optionally substituted by 1-3 of the substituents referred to above for the

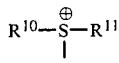

ring; $R^{15}$ is selected from the group consisting of hydrogen; substituted and unsubstituted: alkyl, alkenyl and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; spirocycloalkyl having 3-6 carbon atoms; phenyl; aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hetero atom or atoms in the above-named heterocyclic moieties are selected from the group consisting of 1-4 oxygen, nitrogen and sulfur atoms and the alkyl moieties associated with said heterocyclic moieties have 1-6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieties of the above-recited substituents have 1-6 carbon atoms; and pharmaceutically acceptable salts thereof. The compounds of formula I are potent antibacterial agents or intermediates useful in the preparation of such agents.

Also included in the invention are processes for preparing the novel carbapenem derivatives described above and pharmaceutical compositions containing the biologically active carbapenem derivatives in combination with pharmaceutically acceptable carriers or diluents.

DETAILED DESCRIPTION

The novel compounds of general formula I above contain the carbapenem nucleus

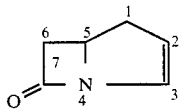

and may thus be named as 1-carba-2-penem-3-carboxylic acid derivatives. Alternatively, the compounds may be considered to have the basic structure

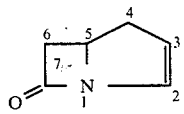

and named as 7-oxo-1-azabicyclo(3.2.0)hept-2-ene-2-carboxylic acid derivatives. While the present invention includes compounds wherein the relative stereochemistry of the 5,6-protons is cis as well as trans, the preferred compounds have the 5R,6S (trans) stereochemistry as in the case of thienamycin.

The compounds of formula I may be unsubstituted in the 6-position or substituted by substituent groups previously disclosed for other carbapenem derivatives. More specifically, $R^8$ may be hydrogen and $R^1$ may be hydrogen or a non-hydrogen substituent disclosed, for example, in European Patent Application 38,869 (see definition of $R_6$). Alternatively, $R^8$ and $R^1$ taken together may be $C_2$-$C_{10}$ alkylidene or $C_2$-$C_{10}$ alkylidene substituted, for example, by hydroxy.

The compounds of formula I may also be unsubstituted at the 1-position ($R^{15}$=H) or substituted by substituent groups previously disclosed for other carbapenem derivatives. More specifically, $R^{15}$ may be hydrogen or any of the non-hydrogen 1-substituents disclosed for example, in European Patent Application 54,917 (see definition of $R^1$ or $R^2$ therein) or in U.S. Pat. No. 4,350,631. Preferred non-hydrogen $R^{15}$ substituents include $C_1$-$C_6$ alkyl, most preferably methyl; phenyl; and phenyl($C_1$-$C_6$)alkyl. The non-hydrogen $R^{15}$ substituent may be in either the α- or β-configuration, and it is intended that the present invention include the individual α- and β-isomers, as well as mixtures thereof. The most preferred 1-substituted compounds are those having the β-configuration, especially those having the β-methyl substituent.

To elaborate on the definitions for $R^1$, $R^8$, and $R^{15}$:

(a) The aliphatic "alkyl", "alkenyl" and "alkynyl" groups may be straight or branched chain having 1-10 carbon atoms; preferred are 1-6, most preferably 1-4, carbon atoms; when part of another substituent, e.g. as in cycloalkylalkyl, or heteroaralkyl or aralkenyl, the alkyl, alkenyl and alkynyl group preferably contains 1-6, most preferably 1-4, carbon atoms.

(b) "heteroaryl" includes mono-, bi- and polycyclic aromatic heterocyclic groups containing 1-4 O, N, or S atoms; preferred are 5- or 6-membered heterocyclic rings such as thienyl, furyl, thiadiazolyl, oxadiazolyl, triazolyl, isothiazolyl, thiazolyl, imidazolyl, isoxazolyl, tetrazolyl, oxazolyl, pyridyl, pyrazinyl, pyrimidinyl, pyridazinyl, pyrrolyl, pyrazolyl, etc.

(c) "heterocyclyl" includes mono-, bi- and polycyclic saturated or unsaturated non-aromatic heterocyclic groups containing 1-4 O, N or S atoms; preferred are 5- or 6-membered heterocyclic rings such as morpholinyl, piperazinyl, piperidyl, pyrazolinyl, pyrazolidinyl, imidazolinyl, imidazolidinyl, pyrrolinyl, pyrrolidinyl, etc.

(d) "halo" (used also to define $R^{10}$ and $R^{11}$) includes chloro, bromo, fluoro and iodo and is preferably chloro or bromo.

The term "conventional readily removable carboxyl protecting group" refers to a known ester group which has been employed to block a carboxyl group during the chemical reaction steps described below and which can be removed, if desired, by methods which do not result in any appreciable destruction of the remaining portion of the molecule, e.g. by chemical or enzymatic hydrolysis, treatment with chemical reducing agents under mild conditions, irradiation with ultraviolet light or catalytic hydrogenation. Examples of such ester protecting groups include benzhydryl, allyl, p-nitrobenzyl, 2-naphthylmethyl, benzyl, trichloroethyl, silyl such as trimethylsilyl, phenacyl, p-methoxybenzyl, acetonyl, o-nitrobenzyl, 4-pyridylmethyl and $C_1$-$C_6$ alkyl such as methyl, ethyl or t-butyl. Included within such protecting groups are those which are hydrolyzed under physiological conditions such as pivaloyloxmethyl, acetoxymethyl, phthalidyl, indanyl and methoxymethyl. A particularly advantageous carboxyl protecting group is p-nitrobenzyl which may be readily removed by catalytic hydrogenolysis.

The pharmaceutically acceptable salts referred to above include the nontoxic acid addition salts, e.g. salts with mineral acids such as hydrochloric, hydrobromic, hydroiodic, phosphoric, sulfuric, etc. and salts with organic acids such as maleic, acetic, citric, succinic, benzoic, tartaric, furmaric, mandelic, ascorbic, lactic, gluconic and malic. Compounds of formula I in the form of acid additions salts may be written as

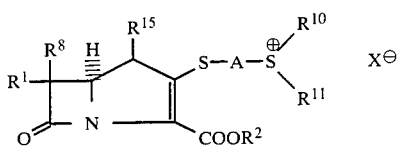

$R^2$=H or protecting group
where $X^\ominus$ represents the acid anion. The counter anion $X^\ominus$ may be selected so as to provide pharmaceutically acceptable salts for therapeutic administration but, in the case of intermediate compounds of formula I, $X^\ominus$ may also be a toxic anion. In such a case the ion can be subsequently removed or substituted by a pharmaceutically acceptable anion to form an active end product for therapeutic use. When acidic or basic groups are present in the $R^1$ group or on the $R^{10}$, $R^{15}$ or $R^{11}$ substituents, the present invention may also include suitable base or acid salts of these functional groups, e.g. acid addition salts in the case of a basic group and metal salts (e.g. sodium, potassium, calcium and aluminum), the ammonium salt and salts with nontoxic amines (e.g. trialkylamines, procaine, dibenzylamine, 1-ephenamine, N-benzyl-$\beta$-phenethylamine, N,N'-dibenzylethylenediamine, etc.) in the case of an acidic group.

Compounds of formula I wherein $R^2$ is hydrogen, an anionic charge or a physiologically hydrolyzable ester group together with pharmaceutically acceptable salts thereof are useful as antibacterial agents. The remaining compounds of formula I are valuable intermediates which can be converted into the above-mentioned biologically active compounds.

A preferred embodiment of the present invention comprises compounds of formula I wherein $R^8$ is hydrogen and $R^1$ is hydrogen, $CH_3CH_2$-,

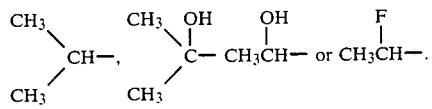

Among this subclass, the preferred compounds are those in which $R^1$ is

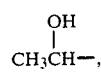

most preferably compounds having the absolute configuration 5R, 6S, 8R.

Another preferred embodiment comprises compounds of formula I in which $R^1$ and $R^8$ taken together form an alkylidene radical of the formula

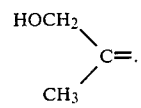

The alkylene (i.e. substituent "A") radical in the compounds of formula I may be straight or branched chain and may contain from 2 to 6 carbon atoms. A preferred embodiment comprises those compounds in which A is —$(CH_2)_n$— in which n is 2, 3 or 4 and a particularly preferred embodiment comprises those compounds where A is —$CH_2CH_2$—.

The 2-substituent of the present compounds is characterized by the presence of a sulfonium group attached to the alkylene radical A. As indicated above, $R^{10}$ and $R^{11}$ may each independently be selected from optionally substituted aliphatic, cycloaliphatic, cycloaliphatic-aliphatic, aryl, heterocyclyl, heterocyclyl-aliphatic heteroaryl or heteroaraliphatic. Alternatively, the $R^{10}$ and $R^{11}$ substituents when taken together with the

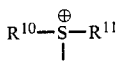

to which they are attached may form a 4-6 membered, optionally substituted, sulfur-containing heterocyclic ring containing 0-2 double bonds and 0-2 additional heteroatoms selected from O, N and S, said ring being attached to A through a sulfur atom, thereby forming a sulfonium group. In the latter case where

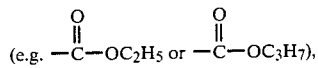

represents a heterocyclic ring, the ring may also be fused to a $C_5$-$C_6$ carbocyclic ring, a phenyl ring or a 5-6 membered heteroaryl ring (containing 1-4 O, N or S) and any of such fused rings may also be optionally substituted.

The aliphatic $R^{10}$ and/or $R^{11}$ substituents are preferably $C_1$-$C_6$ alkyl, $C_2$-$C_6$ alkenyl or $C_2$-$C_6$ alkynyl. Cycloaliphatic substituents are preferbly $C_3$-$C_6$ cycloalkyl while cycloaliphatic-aliphatic refers especially to $C_3$-$C_6$ cycloalkyl-$C_1$-$C_6$ alkyl. Such aliphatic, cycloaliphatic and cycloaliphatic-aliphatic substituents may be unsubstituted or substituted (preferably by 1-4 substituents) by the following: hydroxy, $C_1$-$C_6$ alkoxy, $C_1$-$C_6$ alkanoyloxy, carboxy, $C_1$-$C_6$ alkoxycarbonyl (e.g. —$\overset{O}{\underset{\|}{C}}$—$OC_2H_5$ or —$\overset{O}{\underset{\|}{C}}$—$OC_3H_7$), amino, $C_1$-$C_6$ alkylamino, di($C_1$-$C_6$)alkylamino, $C_1$-$C_6$ alkanoylamino, phenyl, phenyl substituted by, preferably 1-3 and most preferably 1-2, halo, $C_1$-$C_6$ alkoxy, $C_1$-$C_6$ alkyl, carboxy, carboxy-$C_1$-$C_6$ alkyl, amino, $C_1$-$C_6$ alkylamino, di($C_1$-$C_6$)alkylamino or di($C_1$-$C_6$)alkylamino($C_1$-$C_6$)alkyl, halo or oxo.

The $R^{10}$ and/or $R^{11}$ substituents may also be aryl ($C_6$-$C_{10}$ aromatic hydrocarbon) which is most especially phenyl. The aryl group or groups may be unsubstituted or substituted by 1-3, preferably 1-2, substituents selected from halo, $C_1$-$C_6$ alkoxy, $C_1$-$C_6$ alkyl, carboxy, amino, $C_1$-$C_6$ alkylamino and di($C_1$-$C_6$)alkylamino.

When $R^{10}$ and/or $R^{11}$ represent heterocyclyl or heterocyclyl-aliphatic, the heterocyclyl moiety is a 4-6 membered non-aromatic ring containing 1-3 hetero atoms selected from O, N and S. The aliphatic moiety associated with heterocyclyl-aliphatic is preferably $C_1$-$C_6$ alkyl. The heterocyclic ring of such groups may be unsubstituted or substituted by 1-3, preferably 1-2, $C_1$-$C_6$ alkyl or $C_1$-$C_6$ alkoxy substituents.

When $R^{10}$ and/or $R^{11}$ represents heteroaryl or hetero-araliphatic, the heterocyclic moiety is a 5-6 membered aromatic ring containing 1-3 hetero atoms selected from O, N and S and the aliphatic (preferably alkyl) moiety has 1-6 carbon atoms. The heteroaryl ring of such substituents may be unsubstituted or substituted by 1-3, preferably 1-2, substituents selected from $C_1$-$C_6$ alkyl, $C_1$-$C_6$ alkoxy, carboxy, carboxy($C_1$-$C_6$)alkyl, amino, ($C_1$-$C_6$)alkylamino, di($C_1$-$C_6$)alkylamino, amino($C_1$-$C_6$)alkyl and di($C_1$-$C_6$)alkylamino($C_1$-$C_6$)alkyl.

The $R^{10}$ and $R^{11}$ substituents taken together with the $S^{\oplus}$ to which they are attached may also represent a 4-6 member sulfur-containing heterocyclic ring containing 0-2 (preferably 0) double bonds and 0-2 additional heteroatoms selected from O, N, and S, said ring being attached to the alkylene (A) group through a sulfur atom, thereby forming a sulfonium group. The heterocyclic ring formed by

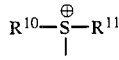

may be unsubstituted or substituted by 1-3, preferably 1-2, substituents selected from:

$C_1$-$C_6$ alkyl optionally substituted by 1-3 hydroxy, $C_1$-$C_6$ alkoxy, carboxy, halo, amino, $C_1$-$C_6$ alkylamino or di($C_1$-$C_6$)alkylamino groups;
hydroxy;
$C_1$-$C_6$ alkoxy;
$C_1$-$C_6$ alkanoyloxy;
amino;
$C_1$-$C_6$ alkylamino;
di($C_1$-$C_6$)alkylamino;
$C_1$-$C_6$ alkanoylamino;
carboxy;
$C_1$-$C_6$ alkoxycarbonyl;
halo;
oxo; and
phenyl.

The heterocyclic ring may also fused to a $C_5$-$C_6$ carbocyclic ring, a phenyl ring, a 5-6 member heterocyclic (containing 1-4 hetero atoms selected from O, N and S) ring or a 5-6 member heteroaryl (containing 1-4 hetero atoms selected from O, N and S) ring, all of which fused rings may be optionally substituted by 1-3, preferably 1-2, of the substituents described above in connection with the sulfur-containing heterocyclic ring.

A preferred embodiment of the present invention comprises compounds of the formula

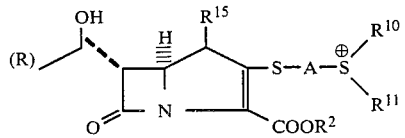

wherein A is $C_2$-$C_6$ straight or branched chain alkylene; $R^2$ is hydrogen, an anionic charge or a conventional readily removable carboxyl protecting group; $R^{15}$ is hydrogen or a β-methyl substituent and $R^{10}$ and $R^{11}$ each independently represents (a) $C_1$-$C_6$ alkyl, $C_2$-$C_6$ alkenyl, $C_2$-$C_6$ alkynyl, $C_3$-$C_6$ cycloalkyl or cycloalkylalkyl having 3-6 carbon atoms in the cycloalkyl ring and 1-6 carbon atoms in the alkyl moiety, said alkyl, alkenyl, alkynyl, cycloalkyl or cycloalkylalkyl group being optionally substituted by 1-3 substituents independently selected from hydroxy, $C_1$-$C_6$ alkoxy, $C_1$-$C_6$ alkanoyloxy, carboxy, $C_1$-$C_6$ alkoxycarbonyl, amino, $C_1$-$C_6$ alkylamino, di($C_1$-$C_6$)alkylamino, $C_1$-$C_6$ alkanoylamino, phenyl, phenyl substituted by 1-3 halo, $C_1$-$C_6$ alkoxy, $C_1$-$C_6$ alkyl, carboxy, carboxy($C_1$-$C_6$)alkyl, amino, $C_1$-$C_6$ alkylamino, di($C_1$-$C_6$)alkylamino or di($C_1$-$C_6$)alkylamino($C_1$-$C_6$)alkyl, halo or oxo;

(b) phenyl optionally substituted by 1-3 halo, $C_1$-$C_6$ alkoxy, $C_1$-$C_6$ alkyl, carboxy, amino, $C_1$-$C_6$ alkylamino or di($C_1$-$C_6$)alkylamino groups;

(c) heterocyclyl or heterocyclylalkyl wherein the heterocyclic moiety is a 4-6 membered ring having 1-3 hetero atoms selected from O, N and S and the alkyl moiety has 1-6 carbon atoms, said heterocyclyl or heterocyclylalkyl ring being optionally substituted by 1-3 $C_1$-$C_6$ alkyl or $C_1$-$C_6$ alkoxy groups; or (d) heteroaryl or heteroaralkyl wherein the heterocyclic moiety is a 5-6 membered aromatic ring having 1-3 hetero atoms selected from O, N and S and the alkyl moiety has 1-6 carbon atoms, said heteroaryl or heteroaralkyl ring being optionally substituted by 1-3 $C_1$-$C_6$ alkyl, $C_1$-$C_6$ alkoxy, carboxy, carboxy($C_1$-$C_6$)alkyl, amino, $C_1$-$C_6$ alkylamino, di($C_1$-$C_6$)alkylamino, amino($C_1$-$C_6$)alkyl or di($C_1$-$C_6$)alkylamino($C_1$-$C_6$)alkyl groups; or wherein $R^{10}$ and $R^{11}$ taken together with the $S^{\oplus}$ to which they are attached represent a 4-6 member sulfur-containing heterocyclic ring containing 0-2 double bonds and 0-2 additional heteroatoms selected from O, N and S, said ring being attached to A through a sulfur atom, thereby forming a sulfonium group, said heterocyclic ring being optionally substituted by 1-3 substituents independently selected from:

$C_1$-$C_6$ alkyl optionally substituted by 1-3 hydroxy, $C_1$-$C_6$ alkoxy, carboxyl, halo, amino, $C_1$-$C_6$ alkylamino or di($C_1$-$C_6$)alkylamino groups, hydroxy, $C_1$-$C_6$ alkoxy, $C_1$-$C_6$ alkanoyloxy, amino, $C_1$-$C_6$ alkylamino, di($C_1$-$C_6$)alkylamino, $C_1$-$C_6$ alkanoylamino, carboxy, $C_1$-$C_6$ alkoxycarbonyl, halo, oxo or phenyl; or wherein said heterocyclic ring

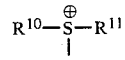

is fused to a $C_5$-$C_6$ carbocyclic ring, a phenyl ring, a 5-6 member heterocyclic ring or a 5-6 member heteroaryl ring, all of which rings may be optionally substituted by 1-3 of the substituents referred to above for the

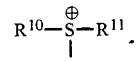

ring; and pharmaceutically acceptable salts thereof.

Within the above group of compounds, a preferred subclass comprises those compounds wherein A is —CH$_2$CH$_2$—.

Another preferred embodiment of the present invention comprises compounds of the formula

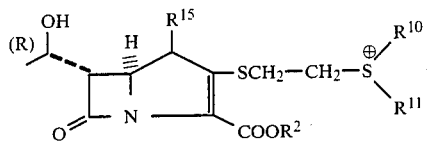

wherein R$^2$ is hydrogen, an anionic charge or a conventional readily removable carboxyl protecting group, R$^{15}$ is hydrogen or β-methyl and

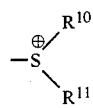

represents

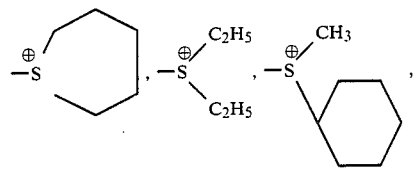

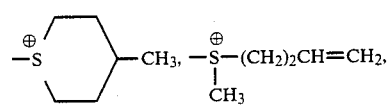

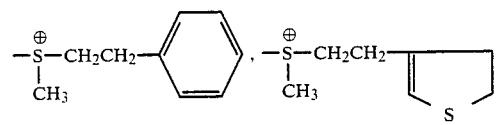

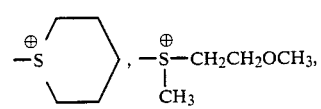

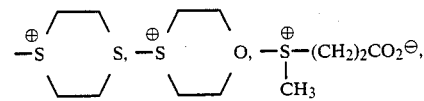

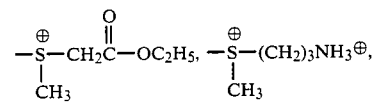

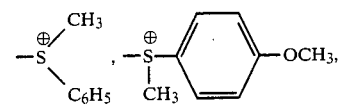

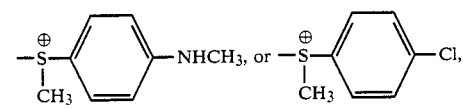

and pharmaceutically acceptable salts thereof.

A particularly preferred embodiment of the present invention comprises compounds of formula I wherein either (a) R$^{10}$ and R$^{11}$ each independently represents C$_1$-C$_6$ alkyl or (b) R$^{10}$ and R$^{11}$ taken together with the S$^\oplus$ to which they are attached represent

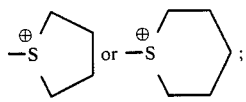

and pharmaceutically acceptable salts thereof.

Examples of preferred 2-substituents wherein R$^{10}$ and R$^{11}$ are alkyl include

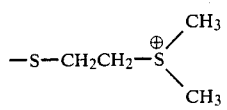

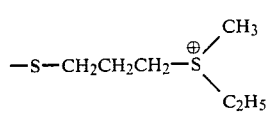

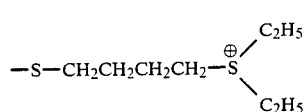

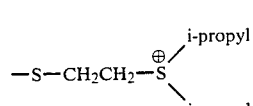

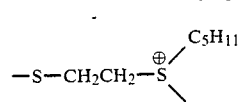

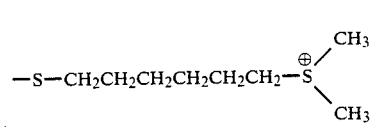

and

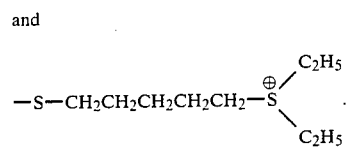

Within this subclass, the preferred compounds are those wherein A is —(CH$_2$)$_n$— in which n is 2, 3 or 4, most preferably those in which A is —CH$_2$CH$_2$— and wherein either (a) R$^1$ and R$^8$ taken together represent

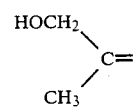

or (b) R$^8$ is hydrogen and R$^1$ represents hydrogen, CH$_3$—CH$_2$—,

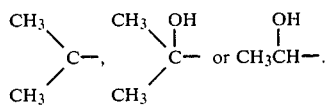

Particularly preferred are the compounds wherein $R^8$ is hydrogen and $R^1$ is

preferably compounds having the absolute configuration 5R, 6S, 8R.

A most preferred embodiment of the present invention comprises compounds of formula I wherein

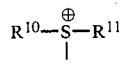

represents

and pharmaceutically acceptable salts thereof. Within this subclass, the preferred compounds are those wherein A is $-(CH_2)_n$ in which n is 2, 3 or 4, most preferably those in which A is $-CH_2CH_2-$ and wherein either (a) $R^1$ and $R^8$ taken together represent

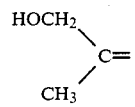

or (b) $R^8$ is hydrogen and $R^1$ represents hydrogen, $CH_3CH_2-$,

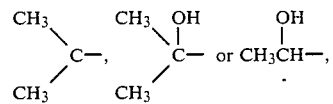

Particularly preferred are the compounds wherein $R^8$ is hydrogen and $R^1$ is

preferably compounds having the absolute configuration 5R, 6S, 8R,

The most preferred embodiment of the present invention comprises the compounds of the formula

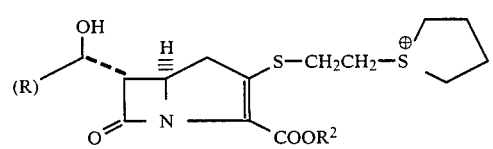

wherein $R^2$ is hydrogen, an anionic charge or a conventional readily removable carboxyl protecting group, providing that when $R^2$ is hydrogen or a protecting group, there is also present a counter anion, and pharmaceutically acceptable acid addition salts thereof.

It will be appreciated that when $R^{10}$ and $R^{11}$ in formula I are different, there may be formed both the R and S optical isomers of such compounds as well as epimeric mixtures thereof. It is intended that the present invention include within its scope all such optical isomers and epimeric mixtures. Similarly, the 6-substituent may in certain cases, e.g. as in hydroxyethyl, be in either the R or S configuration and the resulting isomers as well as epimeric mixtures thereof are encompassed by the present invention.

The carbapenem derivatives of general formula I are prepared from starting materials of the formula

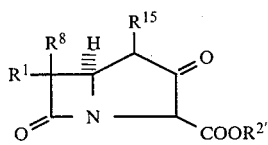

wherein $R^1$, $R^8$, and $R^{15}$ are defined above and wherein $R^{2'}$ represents a conventional readily removable carboxyl protecting groups. Compounds of formula III have been disclosed, for example, in European Patent Application Nos. 38,869 (compound 7), and 54,917 and may be prepared by the general methods described therein.

The process for preparing compounds I from starting materials III may be summarized by the following reaction scheme:

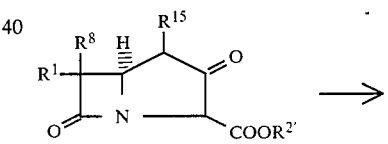

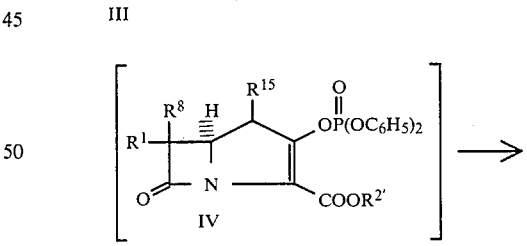

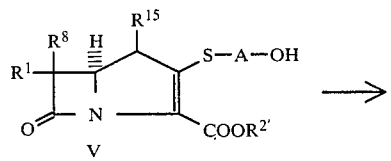

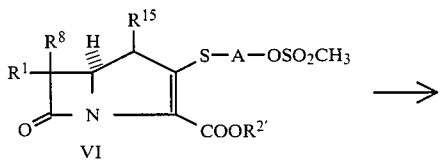

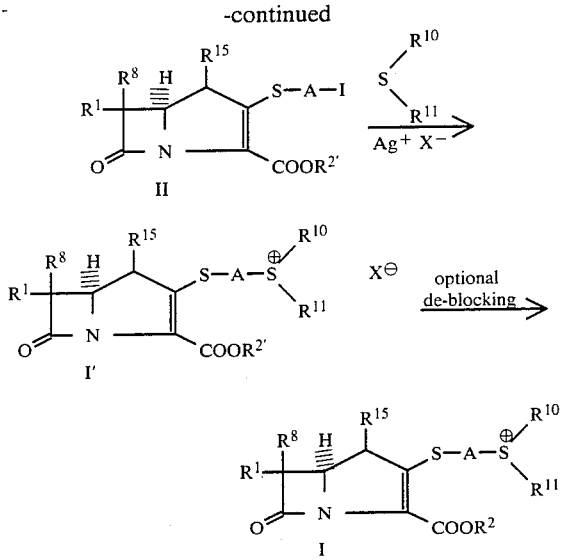

To elaborate on the above process, starting material III is reacted in the inert organic solvent such as methylene chloride, acetonitrile or dimethylformamide with about an equimolar amount of diphenyl chlorophosphate in the presence of a base such as diisopropylethylamine, triethylamine, 4-dimethylaminopyridine or the like to give intermediate IV. The acylation to establish the diphenylphosphoryloxy leaving group at the 2-position of intermediate III is advantageously carried out at a temperature of from about $-20°$ to $+40°$ C., most preferably at about $0°$ C. Intermediate IV may be isolated if desired, but is conveniently used for the next step without isolation or purification.

Intermediate IV is next converted to intermediate V by a conventional displacement reaction. Thus, intermediate IV may be reacted with approximately an equimolar amount of a mercaptan reagent of the formula

HS—A—OH wherein A represents $C_2$–$C_6$ straight or branched chain alkylene in an inert organic solvent such as dioxane, dimethylformamide, dimethylsulfoxide or acetonitrile and in the presence of a base such as diisopropylethylamine, triethylamine, sodium hydrogen carbonate, potassium carbonate or 4-dimethylaminopyridine. The temperature for the displacement is not critical, but an advantageous temperature range is from about $-40°$ C. to $25°$ C. Most conveniently, the reaction is carried out with cooling, e.g. at about $0°$ C.

Intermediate V is then acylated with methanesulfonyl chloride or a functional acylating equivalent thereof such as methanesulfonic acid anhydride in an inert organic solvent and in the presence of base to provide the methanesulfonyloxy leaving group of intermediate VI. The acylation is carried out in an inert organic solvent such as tetrahydrofuran, methylene chloride, acetonitrile or dimethylformamide and in the presence of a suitable base such as diisopropylethylamine, triethylamine, 4-dimethylaminopyridine, and the like. The reaction may be carried out over a wide temperature range, e.g. $-40°$ C. to $+40°$ C., but is most advantageously conducted with cooling, e.g. at about $-30°$ C. to $-40°$ C.

Intermediate VI is next subjected to a displacement reaction so as to provide in intermediate II the iodo leaving group. This particular group has been found to greatly facilitate preparation of the carbapenem end-products of formula I. The intermediates of general formula II, therefore, comprise a preferred embodiment of the present invention.

The displacement of the methanesulfonyloxy leaving group is carried out by reacting intermediate VI with a source of iodide ions in an inert organic solvent such as acetone, dimethylformamide or dimethylsulfoxide. Any compound which ionizes in the solvent employed to provide iodide ions may be used, e.g. an alkali metal iodide such as NaI or KI. The temperature for the displacement is not critical, but temperatures of room temperature or above are most advantageous for achieving completion of the reaction in a reasonable time period. The source of iodide ions is employed in an amount so as to provide approximately an equivalent or excess of iodide ion relative to intermediate VI.

Preparation of the desired carbapenem derivatives of formula I is carried out by a nucleophilic displacement of the iodo leaving group of intermediate II by the desired sulfide of the general formula

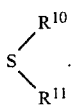

Intermediate II is reacted with at least an equivalent, preferably an excess, of the desired sulfide in an inert organic solvent and in the presence of silver ion. Suitable inert organic solvents include, for example, tetrahydrofuran, dioxane, methylene chloride, diglyme, dimethoxyethane, and the like. Any silver compound which substantially ionizes in the solvent and to give silver ions and an inert anion may be used as the source of silver ion, e.g. $AgClO_4$. Generally, we prefer to use approximately an equivalent amount (relative to intermediate II) of silver ion to facilitate the displacement. The reaction may be carried out over a wide temperature range, e.g. from about $-25°$ C. to about $+25°$ C., but is preferably conducted at around $0°$ C. Intermediate I' will have a counter anion (derived from the silver salt used) associated with it which may at this stage be substituted by a different counter anion, e.g. one which is pharmaceutically acceptable, by conventional procedures. Alternatively, the counter ion may be subsequently removed during the de-blocking step.

The de-blocking step to remove the carboxyl protecting group $R^{2'}$ of intermediate I' is accomplished by conventional procedures such as solvolysis, chemical reduction or hydrogenation. Where a protecting group such as p-nitrobenzyl, benzyl, benzhydryl or 2-naphthylmethyl is used which can be removed by catalytic hydrogenation, intermediate I' in a suitable solvent such as dioxane-water-ethanol, tetrahydrofuran-aqueous dipotassium hydrogen phosphate-isopropanol or the like may be treated under a hydrogen pressure of from 1 to 4 atmospheres in the presence of a hydrogenation catalyst such as palladium on charcoal, palladium hydroxide, platinum oxide or the like at a temperature of from $0°$ to $50°$ C. for from about 0.24 to 4 hours. When $R^{2'}$ is a group such as o-nitrobenzyl, photolysis may also be used for deblocking. Protecting groups such as 2,2,2-trichloroethyl may be removed by mild zinc reduction. Similarly, other conventional carboxyl protecting groups may be removed by methods known to those skilled in the art. Finally, as mentioned above, compounds of formula I' where $R^{2'}$ is a physiologically hydrolyzable ester such as acetoxymethyl, phthalidyl, indanyl, pivaloyloxymethyl, methoxymethyl, etc. may be administered directly to the host without de-blocking since such esters are hydrolyzed in vivo under physiological conditions.

It will be understood that where the $R^1$, $R^{15}$, and/or $R^8$ substituent or the sulfide nucleophile attached to substituent A contain a functional group which might interfere with the intended course of reaction, such group may be protected by a conventional blocking group and then subsequently de-blocked to regenerate the desired functional group. Suitable blocking groups and procedures for introducing and removing such groups are well known to those skilled in the art.

As in the case of other $\beta$-lactam antibiotics, compounds of general formula I may be converted by known procedures to pharmaceutically acceptable salts which, for purposes of the present invention, are substantially equivalent to the non-salted compounds. Thus, for example, one may dissolve a compound of formula I wherein $R^2$ is an anionic charge in a suitable inert solvent and then add an equivalent of a pharmaceutically acceptable acid. The desired acid addition salt may be recovered by conventional procedures, e.g. solvent precipitation, lyophilization, etc. Where other basic or acidic functional groups are present in the compound of formula I, pharmaceutically acceptable base addition salts and acid addition salts may be similarly prepared by known methods.

A compound of formula I where $R^2$ is hydrogen or an anionic charge, or a pharmaceutically acceptable salt thereof may also be converted by conventional procedures to a corresponding compound where $R^2$ is a physiologically hydrolyzable ester group, or a compound of formula I wherein $R^2$ is a conventional carboxyl protecting group may be converted to the corresponding compound where $R^2$ is hydrogen, an anionic charge or a physiologically hydrolyzable ester group, or a pharmaceutically acceptable salt thereof.

The novel carbapenem derivatives of general formula I wherein $R^2$ is hydrogen, an anionic charge or a physiologically hydrolyzable carboxyl protecting group, or the pharmaceutically acceptable salts thereof, are potent antibiotics active against various gram-positive and gram-negative bacteria and they may be used, for example, as animal feed additives for promotion of growth, as preservatives in food, as bactericides in industrial applications, for example in waterbased paint and in the white water of paper mills to inhibit the growth of harmful bacteria and as disinfectants for destroying or inhibiting the growth of harmful bacteria on medical and dental equipment. They are especially useful, however, in the treatment of infectious disease in humans and other animals caused by gram-positive or gram-negative bacteria.

The pharmaceutically active compounds of this invention may be used alone or formulated as pharmaceutical compositions comprising, in addition to the active carbapenem ingredient, a pharmaceutically acceptable carrier or diluent. The compounds may be administered by a variety of means; those of principal interest include: orally, topically or parenterally (intravenous or intramuscular injection). The pharmaceutical compositions may be in solid form such as capsules, tablets, powders, etc. or in liquid form such as solutions, suspensions or emulsions. Compositions for injection, the preferred route of delivery, may be prepared in unit dose form in ampules or in multidose containers and may contain formulatory agents such as suspending, stabilizing and dispersing agents. The compositions may be in ready to use form or in powder form for reconstitution at the time of delivery with a suitable vehicle such as sterile water.

The dosage to be administered depends to a large extent on the particular compound being used, the particular composition formulated, the route of administration, the nature and condition of the host and the particular situs and organism being treated. Selection of the particular preferred dosage and route of application, then, is left to the discretion of the therapist. In general, however, the compounds may be administered parenterally or orally to mammalian hosts in an amount of from about 5 to 200 mg/kg/day. Administration is generally carried out in divided doses, e.g. three to four times a day.

To illustrate the potent broad-spectrum antibacterial activity of the carbapenems of the present invention, both in vitro and in vivo, and the low toxicity of the compounds, biological data is provided below relating to the preferred carbapenem compound of the present invention, i.e. 3-[2-(1-tetrahydrothiophenium)ethylthio]-6$\alpha$-[1-(R)-hydroxyethyl]-7-oxo-1-azabicyclo[3.2.0-]hept-2-ene-2-carboxylate prepared in Example 1.

In Vitro Activity

A sample of the above-identified carbapenem compound after solution in water and dilution with Nutrient Broth was found to exhibit the following Minimum Inhibitory Concentrations (M.I.C.) in mcg/ml versus the indicated microorganisms as determined by overnight incubation at 37° C. by tube dilution. N-Formimidoyl thienamycin was included as a comparison compound.

| | In Vitro Antibacterial Activity of Carbapenem Derivative of Example 1 | | |
|---|---|---|---|
| | | MIC (mcg/ml) | |
| Organism | | New Compound | N—Formmidoyl Thienamycin |
| S. pneumoniae | A-9585 | 0.002 | 0.004 |
| S. pyogenes | A-9604 | 0.004 | 0.001 |
| S. aureus | A-9537 | 0.008 | 0.004 |
| S. aureus +50% serum | A-9537 | 0.03 | 0.016 |
| S. aureus (Pen-res.) | A-9606 | 0.016 | 0.008 |
| S. aureus (Meth-res.) | A15097 | 2 | 0.5 |
| S. faecalis | A20688 | 0.5 | 0.5 |
| E. coli ($10^{-4}$ dil.) | A15119 | 0.03 | 0.016 |
| E. coli ($10^{-3}$) | A15119 | 0.06 | 0.03 |
| E. coli ($10^{-2}$) | A15119 | 0.06 | 0.06 |
| E. coli ($10^{-4}$) | A20341-1 | 0.03 | 0.03 |

In vitro antibacterial activity of carbapenem derivatives of Example 1—continued

| | | MIC (mcg/ml) | |
|---|---|---|---|
| Organism | | New Compound | N—Formimidoyl Thienamycin |
| E. coli | A20341-1 | 0.03 | 0.03 |

-continued

| Organism | | MIC (mcg/ml) | |
|---|---|---|---|
| | | New Compound | N—Formimidoyl Thienamycin |
| $(10^{-3})$ | | | |
| E. coli | A20341-1 | 0.06 | 0.13 |
| $(10^{-2})$ | | | |
| K. pneumoniae | A-9664 | 0.06 | 0.13 |
| K. pneumoniae | A20468 | 0.13 | 0.06 |
| P. mirabilis | A-9900 | 0.13 | 0.06 |
| P. vulgaris | A21559 | 0.03 | 0.03 |
| P. morganii | A15153 | 0.06 | 0.13 |
| P. rettgeri | A22424 | 0.25 | 0.25 |
| S. marcescens | A20019 | 0.06 | 0.03 |
| E. cloacae | A-9659 | 0.13 | 0.06 |
| E. cloacae | A-9656 | 0.13 | 0.06 |
| P. aeruginosa | A-9843A | 1 | 1 |
| P. aeruginosa | A21213 | 0.25 | 0.25 |
| H. influenzae | A-9833 | 8 | 16 |
| H. influenzae | A20178 | 8 | 32 |
| H. influenzae | A21518 | 8 | 32 |
| H. influenzae | A21522 | 8 | 32 |
| B. fragilis | A22862 | 0.06 | 0.016 |
| B. fragilis | A22053 | 0.06 | 0.06 |
| B. fragilis | A22696 | 0.25 | 0.13 |
| B. fragilis | A22863 | 0.06 | 1 |

In Vivo Activity

The in vivo therapeutic efficacy of the compound of Example 1 and N-formimidoyl thienamycin after intramuscular administration to mice experimentally infected with various organisms is shown in the following Table. The $PD_{50}$ (dose in mg/kg required to give protection to 50% of the infected mice) is indicated.

| Protective Effect in the Intramuscular Treatment of Infected Mice | | | |
|---|---|---|---|
| | | PD$_{50}$/Treatment (mg/kg) | |
| Organism | Challenge (No. of organisms) | Compound of Example 1 | N—Formimdoyl Thienamycin |
| S. aureus | A-9606 | $1 \times 10^9$ | 0.19 | 0.07* |
| E. coli | A15119 | $6 \times 10^6$ | 1.6 | 2.2* |
| K. pneumoniae | A-9664 | $7 \times 10^6$ | 5 | 2.4* |
| E. cloacae | A-9659 | $4 \times 10^6$ | 1.3 | — |
| P. mirabilis | A-9900 | $4 \times 10^6$ | 7.7 | 3*/15* |
| P. vulgaris | A21559 | $4 \times 10^5$ | 3.3 | — |
| P. rettgeri | A15167-2 | $3 \times 10^7$ | 8.7 | 6.9 |
| M. morganii | A15149 | $7 \times 10^5$ | 3.3 | — |
| S. marcescens | A20335 | $9 \times 10^6$ | 5 | — |
| P. aeruginosa | A-9843a | $3 \times 10^4$ | 0.6 | 0.5* |
| P. aeruginosa | A20481 | $3 \times 10^4$ | 0.8 | 0.4 |
| P. aeruginosa | A20599 | $9 \times 10^4$ | 1.3 | — |

*Historical data
Treatment Schedule: Mice were treated i.m. with drugs 0 and 2 hours post-infection (A21559, A15167-2, A9900, A9843a, A20481, A20599), or 1 and 3.5 hours (all others); 5 mice were used in each test.

Toxicity

The toxicity of the compound of Example 1 after intracranial administration to mice was determined and is shown in the following Table.

| | Toxicity After Intracranial Administration to Mice | |
|---|---|---|
| Compound | *LD$_{50}$ (mg/kg) | Highest Dose (mg/kg) Without Clinical Signs of Toxicity |
| Compound of Example 1 | >40 | ~5 |
| N—Formimidoyl Thienamycin | 32 | ~5 |

*Average of 25 mice/compound

Blood Levels in Mice After Intramuscular Administration

Blood levels and the half-life of the compound of Example 1 after intramuscular administration of 20 mg/kg in mice are shown in the Table below.

| Compound | Blood Level (μg/ml) | | | | | | *t$_{\frac{1}{2}}$ (min) | **AUC (μg.h/ml) |
|---|---|---|---|---|---|---|---|---|
| | 10 | 20 | 30 | 45 | 60 | 90 | | |
| | Minutes after Administration | | | | | | | |
| Compound of Example 1 | 14.7 | 13.5 | 8.7 | 3.2 | 0.9 | <0.6 | 9 | 7.4 |
| N—Formimidoyl Thienamycin | 12.6 | 9.9 | 7.3 | 2.6 | 0.7 | <0.3 | 9 | 6 |

Compounds were solubilized in 0.1 M phosphate buffer pH 7. Values are from a single test; 4 mice used per compound.
*t$_{\frac{1}{2}}$ refers to half-life in minutes
**AUC refers to the area under the curve

Urinary Recovery

The urinary recovery of the compound of Example 1 after intramuscular administration (20 mg/kg) to mice is shown in the following Table.

| | Urinary Recovery Intramuscular Administration of 20 mg/kg to Mice | | | |
|---|---|---|---|---|
| | Percentage of Dose Recovered | | | |
| Compound | 0–3 | 3–6 | 6–24 | 0–24 |
| | Hours After Administration | | | |
| Compound of Example 1 | 15.6 | 2.1 | <0.2 | 17.7 ± 2.9 |
| N—Formimidoyl Thienamycin | 12.1 | 0.1 | <0.1 | 12.2 ± 3.6 |

Compounds were solubilized in 0.1 M phosphate buffer pH 7. Values are from a single test; 4 mice per compound.

The following examples illustrate but do not limit the scope of the present invention.

EXAMPLE 1

Preparation of 3-[2-(1-tetrahydrothiophenium)ethylthio]-6α-[1-(R)-hydroxyethyl]-7-oxo-1-azabicyclo[3.2.0]hept-2-ene-2-carboxylate

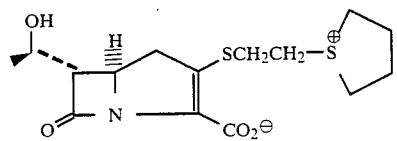

A. p-Nitrobenzyl 3-(2-hydroxyethylthio)-6α-[1-(R)-hydroxyethyl]-7-oxo-1-azabicyclo[3.2.0]hept-2-ene-2-carboxylate

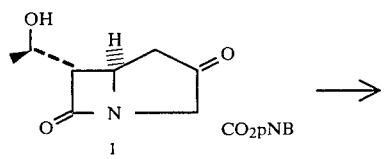

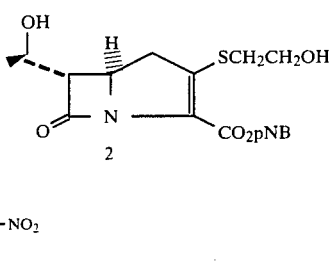

A solution of 1.69 g (4.85 mmole) of p-nitrobenzyl 6α-[1-(R)-hydroxyethyl]-3,7-dioxo-1-azabicyclo(3.2.0-)hept-2-ene-2-carboxylate (1) in 20 ml of acetonitrile was cooled to 0° C. under a nitrogen atmosphere. A solution of 726 mg (7.18 mmole) of diisopropylethylamine in 2 ml of acetonitrile was added followed by a dropwise addition of 1.51 g (5.60 mmole) of diphenyl chlorophosphate in 12 ml of acetonitrile over a period of 3 minutes. The resulting solution was stirred at 0° for 20 minutes to provide p-nitrobenzyl 3-(diphenylphosphoryloxy)-6α-(1-(R)-hydroxyethyl]-7-oxo-1-azabicyclo(3.2.0)hept-2-ene-2-carboxylate. To this solution was added a solution of 726 mg (7.18 mmole) of diisopropylethylamine in 2 ml of acetonitrile followed by a solution of 439 mg (5.63 mmole) of 2-mercaptoethanol in 2 ml of acetonitrile. The reaction solution was stirred at 0° C. for 3 hours and then diluted with 200 ml of ethyl acetate and washed with 200 ml of water, 100 ml of 20% aqueous H$_3$PO$_4$, and brine. Evaporation of the dried (MgSO$_4$) solution gave a semisolid which was triturated with methylene chloride and filtered to yield 1.2 g (61% yield) of title product 2 as a white amorphous solid.

NMR (DMSO-d6) δ: 1.20 (3H, d, J=6.0 Hz), 2.9–3.2 (9H, m), 5.22(1H, d, J=8.5 Hz) and 8.23 (2H, d, J=8.5 Hz); ir (KBr) γmax: 3500, 1770 and 1700 cm$^{-1}$; Anal. Calc'd for C$_{18}$H$_{20}$N$_2$O$_7$S: C, 52.93; H, 4.94; N, 6.86; S, 7.85. Found: C, 52.83; H, 4.90; N, 6.42; S, 8.31.

B. p-Nitrobenzyl 3-(2-methanesulfonyloxyethylthio)-6α-[1-(R)-hydroxyethyl]-7-oxo-1-azabicyclo(3.2.0)hept-2-ene-2-carboxylate

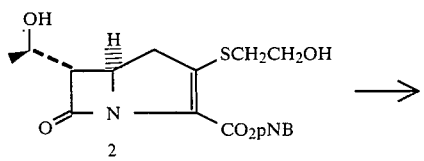

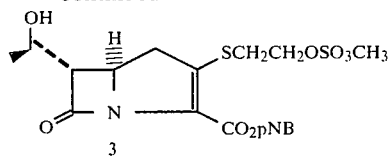

To a solution of 4.2 g (10.3 mmole) of 2 in 200 ml of tetrahydrofuran there was added at −40° C. 1.3 g (11.3 mmole) of methanesulfonyl chloride followed by a dropwise addition of 1.26 g (12.4 mmole) of triethylamine in 5 ml of tetrahydrofuran. The reaction mixture was stirred for 5 hours at −40° C., then stirred for 2 hours at −30° C. under a nitrogen atmosphere and then poured into a mixture of ethyl acetate (700 ml) and 5% aqueous phosphoric acid (1000 ml). The organic layer was washed with brine, dried over MgSO$_4$, filtered and condensed to a syrup. This material was purified by silica gel column chromatography [elution with methylene chloride-ethyl acetate (3:1 v/v)] to give 3.55 g (75% yield) of the title compound as a white amorphous solid.

NMR (CDCl$_3$) δ: 1.25 (3H, d, J=6.0 Hz), 3.05 (3H, s), 3.06–3.40 (5H, m), 4.05–4.40 (4H, m), 5.25 (1H, d J=14.0 Hz), 5.50 (1H, d, J=14.0 Hz), 7.70 (2H, d, J=8.5 Hz) and 8.23 (2H, d, J=8.5 Hz); ir (KBr) γmax: 3400, 1770 and 1600 cm$^{-1}$. Anal. Calc'd for C$_{19}$H$_{22}$N$_2$O$_9$S$_2$: C, 46.90; H, 4.56; N, 5.76. Found: C, 46.52; H, 4.32; N, 5.91.

C. p-Nitrobenzyl 3-(2-iodoethylthio)-6α-[1-(R)-hydroxyethyl]-7-oxo-1-azabicyclo(3.2.0)hept-2-ene-2-carboxylate

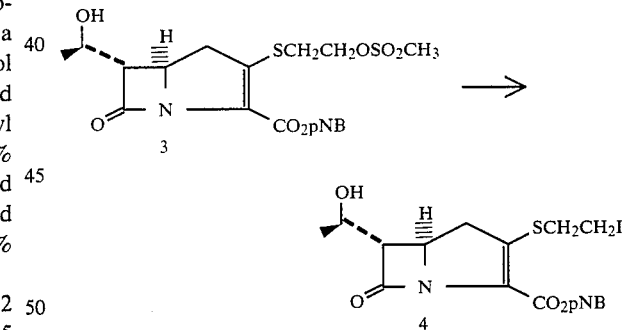

A solution of 350 mg (0.72 mmole) of intermediate 3 and 216 mg (1.4 mmole) of sodium iodide in 20 ml of acetone was heated at reflux for 4 hours. Evaporation of the acetone gave a white amorphous solid which was suspended in ether (10 m)-water (10 ml). Filtration of the white solid and vacuum drying produced 300 mg (80% yield) of the title compound 4 as a white amorphous powder.

NMR (DMSO-d6) δ: 1.18 (3H, d, J=6.0 Hz), 3.20–3.60 (7H, m), 3.80–4.25 (2H, m), 5.10 (1H, d, J=5.5 Hz), 5.25 (1H, d, J=12.0 Hz), 5.45 (1H, d, J=12.0 Hz), 7.70 (2H, d, J=8.5 Hz), and 8.27 (2H, d, J=8.5 Hz); ir (KBr) γmax: 3500, 1768 and 1700 cm$^{-1}$; Anal. Calc'd for C$_{18}$H$_{19}$N$_2$O$_6$I: C, 41.71; H, 3.70; N, 5.41; I, 24.48. Found: C, 42.10; H, 3.75; N, 5.97; I, 23.20.

D.
3-[2-(1-Tetrahydrothiophenium)ethylthio]-6α-[1-(R)-hydroxyethyl]-7-oxo-1-azabicyclo[3.2.0]hept-2-ene-2-carboxylate

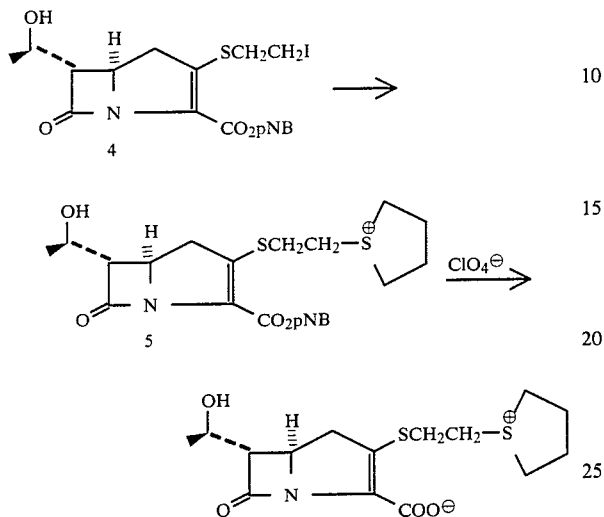

To a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in 5 ml of tetrahydrofuran there was added tetrahydrothiophene (0.3 ml; 0.35 mmole) followed by a solution of silver perchlorate (60 mg; 0.3 mmole) in 0.5 ml of tetrahydrofuran. The mixture was stirred at room temperature for 60 minutes. The solvent was evaporated in vacuo affording compound 5 as a yellow gum. This gum was digested with 100 ml of CELITE to give an amorphous solid.

IR (KBr) γmax: 3400, 1772, 1700 and 1100 cm$^{-1}$. Without any further purification, compound 5 was hydrogenated as follows: To a suspended solution of compound 5 in 20 ml of ether and 20 ml of tetrahydrofuran there was added a solution of potassium bicarbonate (40 mg; 0.4 mmole) and dibasic potassium phosphate (35 mg; 0.2 mmole) in 20 ml of water. Then, 120 mg of 10% palladium on charcoal was added and the mixture was hydrogenated at 40 psi on the Parr Shaker for 60 minutes. The mixture was then filtered and the catalyst was washed with water (2×5 ml). The combined filtrate and washing was extracted with ether (2×50 ml) and then lyophilized to give a yellow powder. This crude material was purified on a $C_{18}$ BONDAPAK reverse phase column (7 g) (Waters Associates), eluting with water under a 8 psi pressure. Each fraction (15 ml) was screened by high pressure liquid chromatography, and fractions having an ultraviolet absorption $\lambda_{max}$ 300 nm were collected and lyophilized to give 12 mg (18% yield based on compound 4) of title product as a white solid.

NMR (D$_2$O) δ: 1.23 (3H, d J=6.0 Hz), 2.25–2.45 (4H, m), 3.0–3.70 (11H, m), 3.95–4.30 (2H, m); ir (KBr) γmax: 3400, 1760 and 1590 cm$^{-1}$. UV $\lambda_{max}$ (CH$_2$CH$_2$OH) 289 nm (ε=6200).

EXAMPLE 2

Preparation of 3-[2-(Diethylsulfonium)ethylthio]-6α-[1-(R)-hydroxyethyl]-7-oxo-1-azabicyclo[3.2.0]hept-2-ene-2-carboxylate

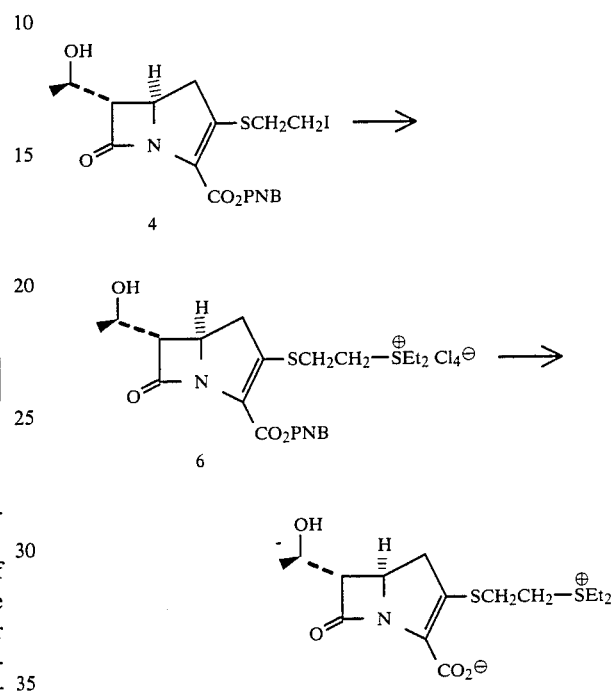

Ethylsulfide (0.04 mL, 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104mg; 0.2 mmole) in tetrahydrofuran (5 mL) followed by a solution of silver perchlorate (60 mg; 0.3 mmole) in tetrahydrofuran (0.5 mL). After stirring at room temperature for 1 h, the solvent is removed to leave crude 6. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining these fractions which absorb at 290 nm followed by lyophilization gives the title compound.

EXAMPLE 3

Preparation of
3-{2-[Cyclohexyl(methyl)sulfonium]ethylthio}-6α-[1-(R)-hydroxyethyl]-7-oxo-1-azebicyclo[3.2.0]hept-2-ene-2-carboxylate

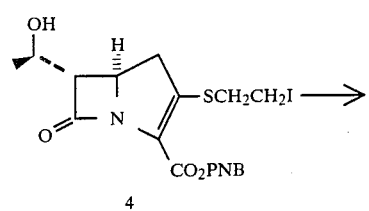
4

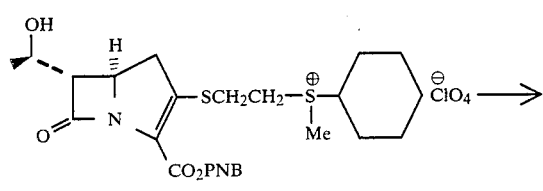
7

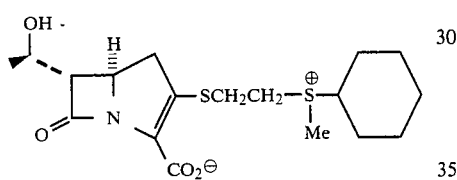

Cyclohexylmethyl sulfide (46 mg, 0.35 mmol) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 1 h, the solvent is removed to leave crude 7. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 4

Preparation of
3-[2-(4-Methyl-1-tetrahydrothiopyranium)ethylthio]-6α-[1-(R)-hydroxyethyl]-7-oxo-1-azabicyclo[3.2.0]hept-2-ene-2-carboxylate

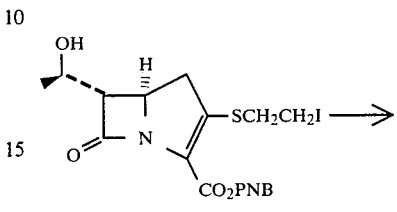
4

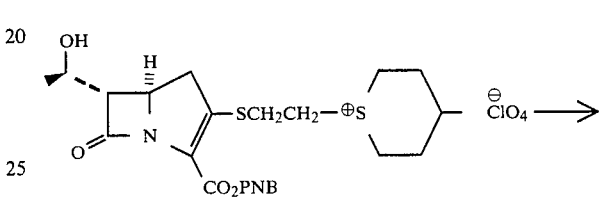
8

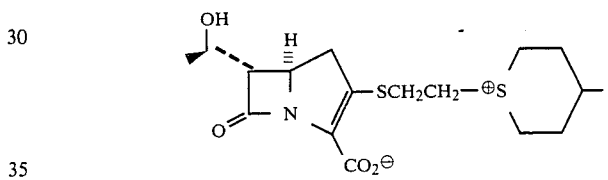

4-Methyl-tetrahydrothiopyran (41 mg, 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 1 h, the solvent is removed to leave crude 8. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed wit water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 5

Preparation of 3-[2-[(4-But-1-enyl)methylsulfonium]ethylthio]-6α-[1-(R)-hydroxyethyl]-7-oxo-1-azabicyclo[3.2.0]hept-2-ene-2-carboxylate

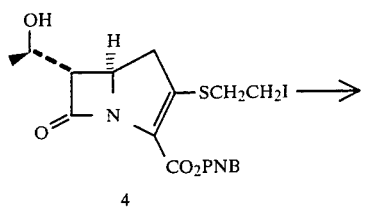

4

EXAMPLE 6

Preparation of 3-[2-[Methyl(2-phenylethyl)sulfonium]ethylthio]-6α-[1-(R)-hydroxyethyl]-7-oxo-1-azabicyclo[3.2.0]hept-2-ene-2-carboxylate

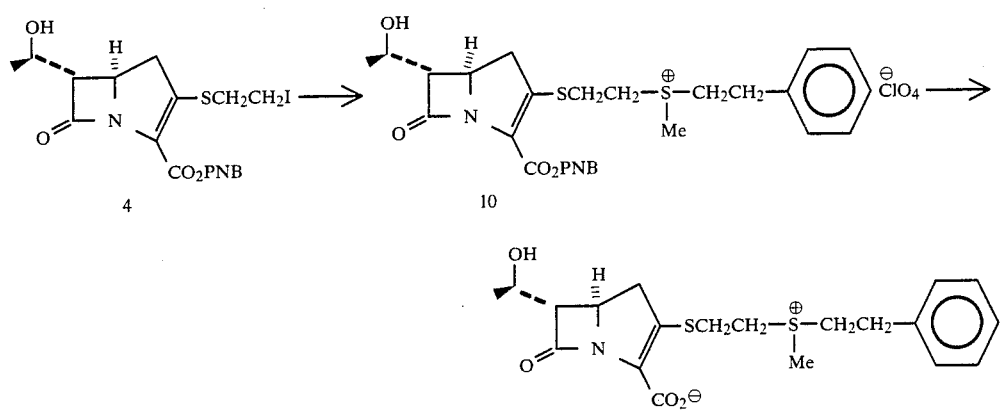

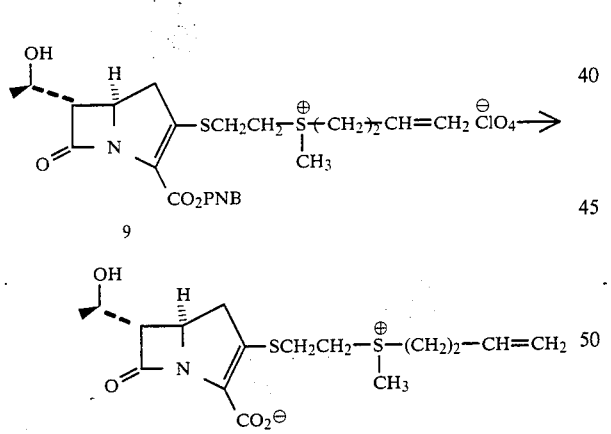

(4-But-1-enyl)methyl sulfide (36 mg, 0.35 mmole is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 1 h, the solvent is removed to leave crude 9. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAk reversed phase column (7 g, Waters Associates), eluting with water under a pressure of 8 psi. Combining those fractions which absorb at 290 nm followed by lyophilization gives the title compound.

Methyl(2-phenylethyl)sulfide (53 mg; 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 1 h, the solvent is removed to leave crude 10. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 7

Preparation of
3-{[(2-{[2-[2-(4,5-Dihydrothienyl)ethyl]methylsulfonium]}-ethylthio)]}-6α-[1-(R)-hydroxyethyl]-7-oxo-1-azabicyclo[3.2.0]hept-2-ene-2-carboxylate

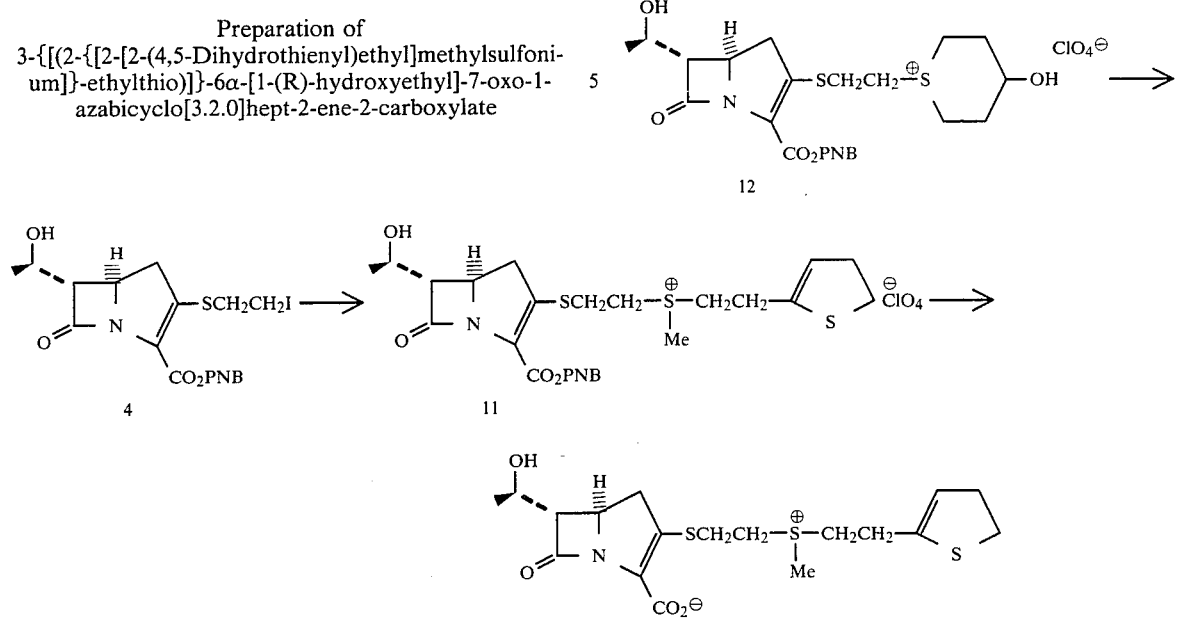

2-(2-Thiomethylethyl)-4,5-dihydrothiophene (56 mg, 0.35 mmole) is added to a solution of p-nitrobenzyl 3-(2-iodoethylthio) 6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 1 h, the solvent is removed to leave crude 11. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 8

Preparation of
3-[2-(4-Hydroxy-1-tetrahydrothiopyranium)ethylthio]-6α-[1-(R)-hydroxyethyl]-7-oxo-1-azabicyclo[3.2.0]hept-2-ene-2-carboxylate

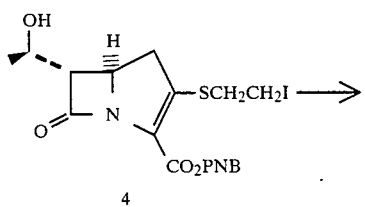

4-hydroxy-tetrahydro-2H-thiopyran (41 mg, 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 1 h, the solvent is removed to leave crude 12. This is taken directly and hydrogenated in the following manner. The compound is a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLES 9

Preparation of
3-[2-[1-(2-Methoxyethyl)methylsulfonium]ethylthio]-6α-[1-(R)-hydroxyethyl]-7-oxo-1-azabicyclo[3.2.0]hept-2-ene-2-carboxylate

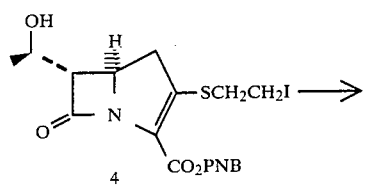

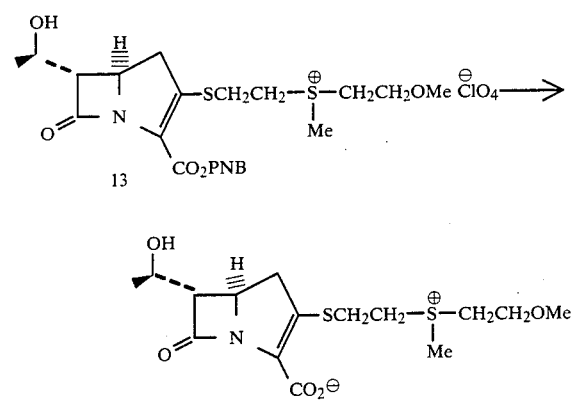

1-(2-Methoxyethyl)-methylsulfide (37 mg, 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 1 h, the solvent is removed to leave crude 13. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 10

Preparation of
3-[2-[1-(1,4-Dithianium)]ethylthio]-6α-[1-(R)-hydroxyethyl]-7-oxo-1-azabicyclo[3.2.0]hept-2-ene-2-carboxylate

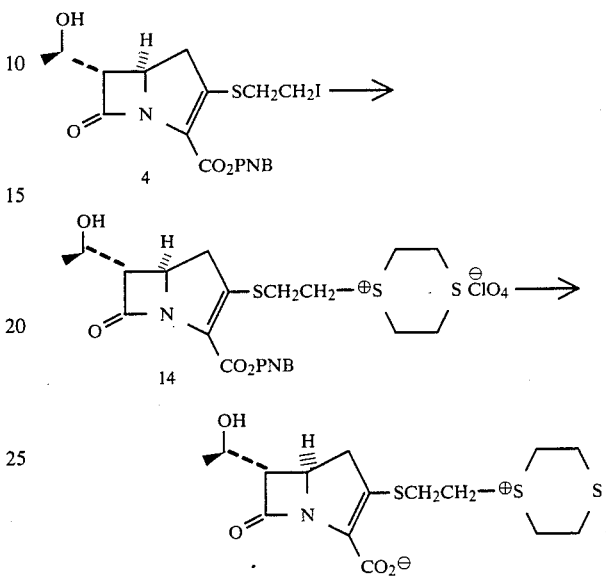

1,4-Dithiane (42 mg, 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 1 h, the solvent is removed to leave crude 14. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 (104 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 11

Preparation of
3-[2-[4-(1,4-Oxathianium)]ethylthio]-6α-[1-(R)-hydroxyethyl]-7-oxo-1-azabicyclo[3.2.0]hept-2-ene-2-carboxylate

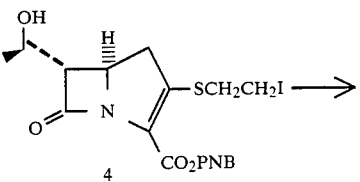

-continued

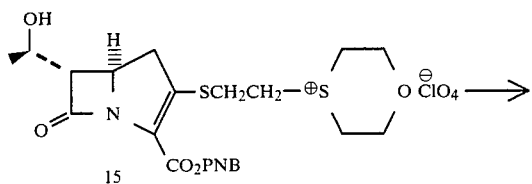

EXAMPLE 12

Preparation of the Potassium Salt of 3-[2-[(Carboxylatoethyl)methylsulfonium]ethylthio]-6α-[1-(R)-hydroxyethyl]-7-oxo-1-azabicyclo[3.2.0]hept-2-ene-2-carboxylate

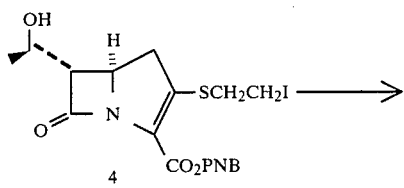

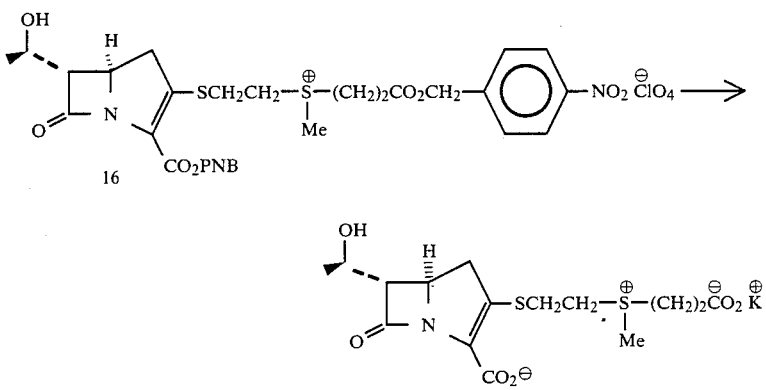

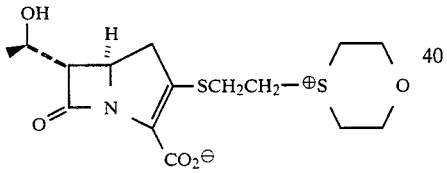

1,4-Oxathiane (0.33 mL, 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 1 h, the solvent is removed to leave crude 15. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

p-Nitrobenzyl(3-thiomethyl)propanoate (89 mg; 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 2 h, the solvent is removed to leave crude 16. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 13

Preparation of
3-[2-[Methyl(ethoxycarbonylmethyl)sulfonium]ethylthio]-6α-[1-(R)-hydroxyethyl]-7-oxo-1-azabicyclo[3.2.0]hept-2-ene-2-carboxylate

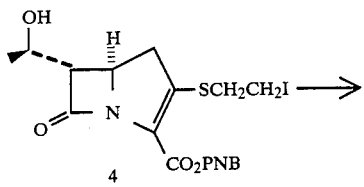

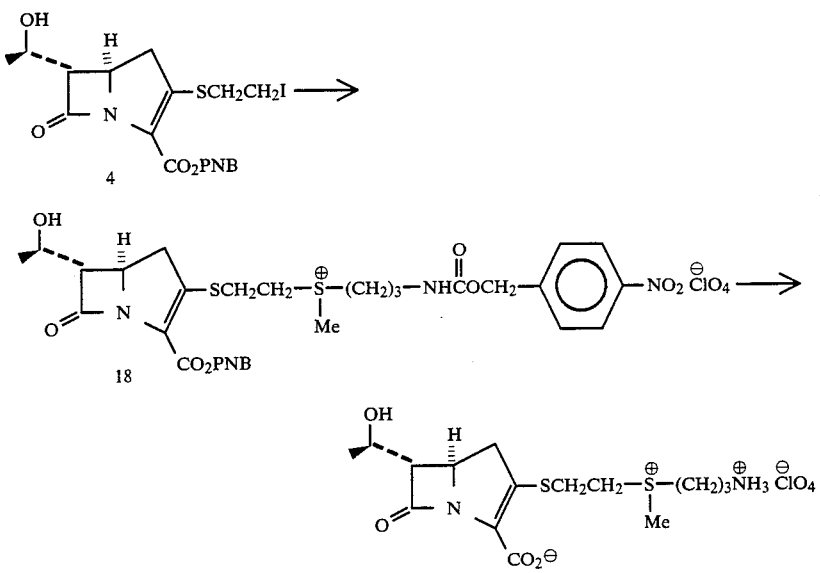

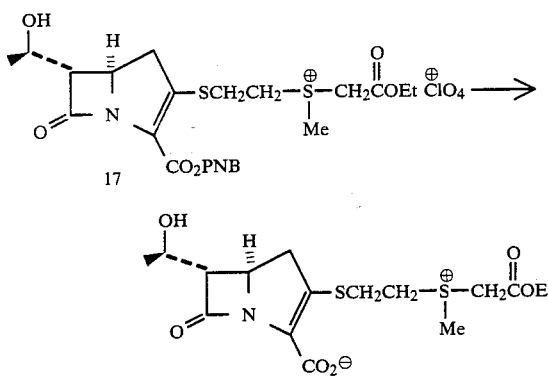

Ethyl(methylthio)acetate (47 mg, 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 1 h, the solvent is removed to leave crude 17. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 14

Preparation of the Perchlorate salt of
3-[2-[Methyl(3-propanaminium)-sulfonium]ethylthio]-6α-[1-(R)-hydroxyethyl]-7-oxo-1-azabicyclo[3.2.0]hept-2-ene-2-carboxylate p-Nitrobenzyl N-(3-thiomethylpropyl)carbamate (99 mg; 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 1 hr, the solvent is removed to leave crude 18. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 15

Preparation of 3-[2-(Methylphenylsulfonium)ethylthio]-6α-[1-(R)-hydroxyethyl]-7-oxo-1-azabicyclo[3.2.0]hept-2-ene-2-carboxylate

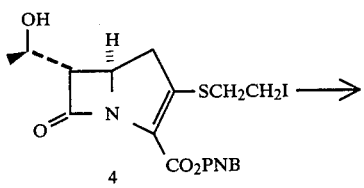

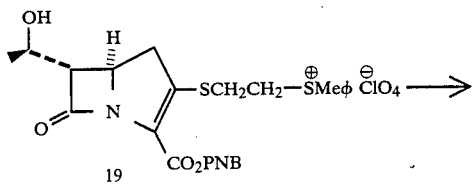

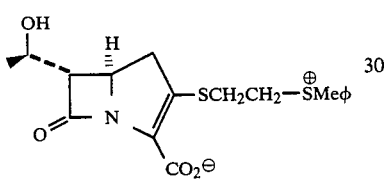

Thioanisole (0.04 mL; 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 2 h, the solvent is removed to leave crude 19. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 16

Preparation of 3-[2-[Methyl(4-methoxyphenyl)sulfonium]ethylthio]-6α-[1-(R)-hydroxyethyl]-7-oxo-1-azabicyclo[3.2.0]hept-2-ene-2-carboxylate

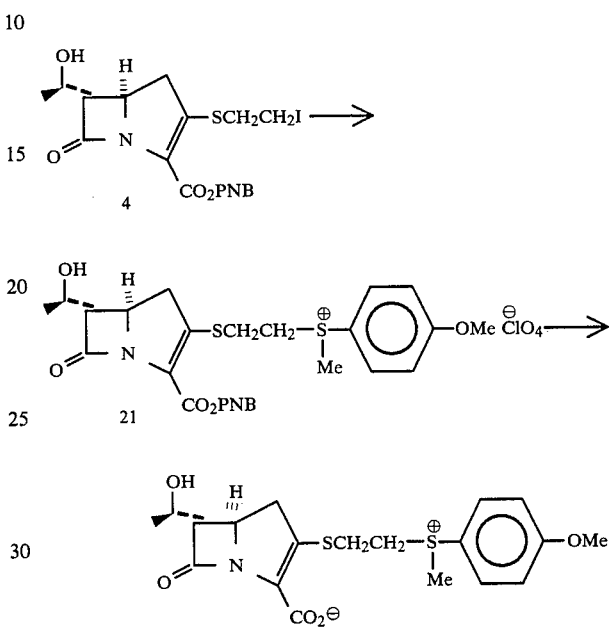

Methyl(4-methoxyphenyl)sulfide (54 mg; 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 2 h, the solvent is removed to leave crude 21. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 17

Preparation of
3-[2-[Methyl[4-(N-methylamino)phenyl]sulfonium]ethylthio]-6α-[1-(R)-hydroxyethyl]-7-oxo-1-azabicyclo[3.2.0]hept-2-ene-2-carboxylate

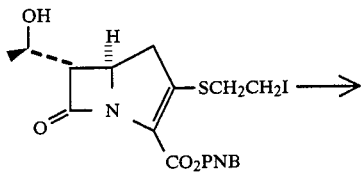

4

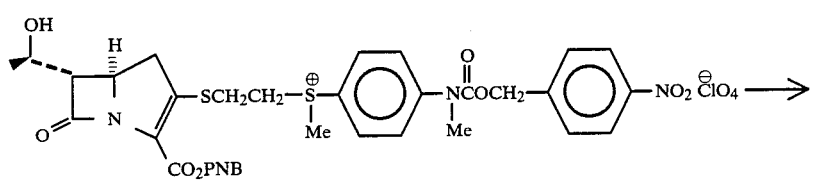

22

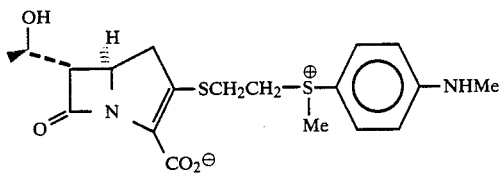

p-Nitrobenzyl N-methyl-N-(p-thiomethylphenyl)carbamate (116 mg; 0.35 mole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 2 h, the solvent is removed to leave crude 22. This is taken directly and hydrogenated in the following manner. The compound in a mixture of ether (20 mL), tetra-hydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 18

Preparation of
3-[2-[p-Chlorophenyl(methyl)sulfonium]ethylthio]-6α-[1-(R)-hydroxyethyl]-7-oxo-1-azabicyclo[3.2.0]hept-2-ene-2-carboxylate

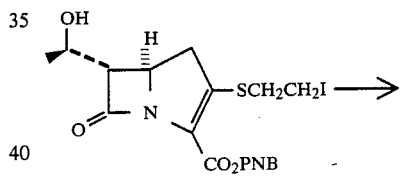

4

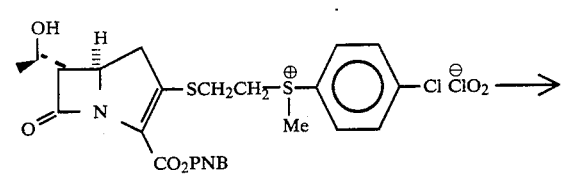

23

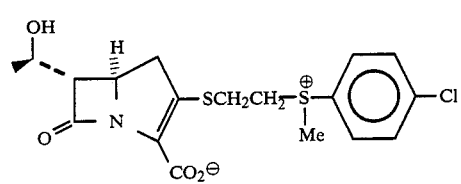

p-Chlorothioanisole (56 mg; 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silverperchlorate (60 mg; 0.3 mmole) in tetrahydrofuran (0.5 mL). After stirring at room temperature for 2 h, the solvent is removed to leave crude 23. This is taken directly and hydrogenated in the following manner. The compound in a mixture of ether (20 mL), tetrahydrofuran (20 mL), water (20 mL)

containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a C$_{18}$ BONDAPAK reversed phase column (7 g, Waters Associates), eluting with water under a pressure of 8 psi. Combining those fractions which absorb at 290 nm followed by lyophilization gives the title compound.

EXAMPLE 19

Preparation of 3-[2-(1-Tetrahydrothiophenium)ethylthio]-6α-[1-(R)-hydroxyethyl]-4β-methyl-7-oxo-1-azabicyclo[3.2.0-]hept-2-ene-2-carboxylate

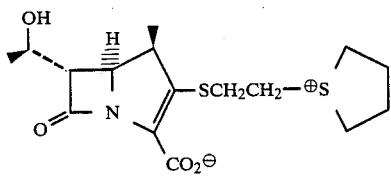

A. p-Nitrobenzyl 3-(2-Hydroxyethylthio)-6α-[1-(R)-hydroxyethyl]-4β-methyl-7-oxo-1-azabicyclo[3.2.0]hept-2-ene-2-carboxylate

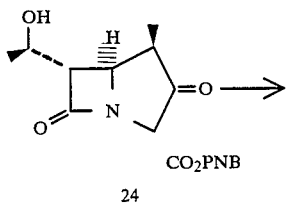

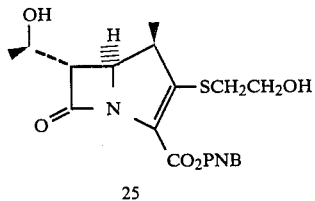

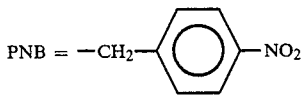

A solution of 1.75 g (4.85 mmole) of p-nitrobenzyl 6α-[1-(R)-hydroxyethyl]-3,7-dioxo-4β-methyl-1-azabicyclo(3.2.0)hept-2-ene-2-carboxylate (24) in 20 mL of acetonitrile is cooled to 0° C. under a nitrogen atmosphere. A solution of 726 mg (7.18 mmole) of diisopropylethylamine is 2 mL of acetonitrile is added followed by a dropwise addition of 1.51 g (5.60 mmole) of diphenyl chlorophosphate in 12 mL of acetonitrile over a period of 3 minutes. The resulting solution is stirred at 0° for 20 minutes to provide p-nitrobenzyl 3-(diphenylphosphoryloxy)-6α-[1-(R)-hydroxyethyl]-4β-methyl-7-oxo-1-azabicyclo[3.2.0]hept-2-ene-2-carboxylate. To this solution is added a solution of 726 mg (7.18 mmole) of diisopropylethylamine in 2 mL of acetonitrile followed by a solution of 439 mg (5.63 mmole) of 2-mercaptoethanol in 2 mL of acetonitrile. The reaction solution is stirred at 0° C. for 3 hours and then diluted with 200 mL of ethyl acetate and washed with 200 mL of water, 100 mL of 20% aqueous H$_3$PO$_4$, and brine. Evaporation of the dried (MgSO$_4$) solution gives the title compound 25.

B. p-Nitrobenzyl 3-(2-Methanesulfonyloxyethylthio)-6α-[1-(R)-hydroxyethyl]-4β-methyl-7-oxo-1-azabicyclo[3.2.0]hept-2-ene-2-carboxylate

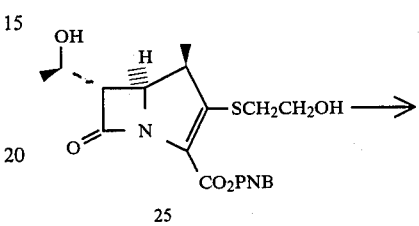

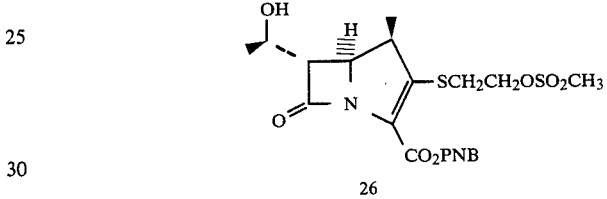

To a solution of 4.5 g (10.3 mmole) of 25 in 200 mL of tetrahydrofuran is added to −40° C., 1.3 g (11.3 mmole) of methanesulfonyl chloride followed by a dropwise addition of 1.26 g (12.4 mmole) of triethylamine in 5 mL of tetrahydrofuran. The reaction mixture is stirred for 5 hours at −40° C., and then 2 hours at −30° C. under a nitrogen atmosphere. It is then poured into a mixture of ethyl acetate (700 mL) and 5% aqueous phosphoric acid (1000 mL). The organic layer is washed with brine, dried over MgSO$_4$, filtered and condensed to a syrup. This material was purified by silica gel column chromatography [elution with methylene chloride-ethyl acetate (3:1 v/v)] to give the title compound 26.

C. p-Nitrobenzyl3-(2-Iodoethylthio)-6α-[1-(R)-hydroxyethyl]-4β-methyl-7-oxo-1-azabicyclo[3.2.0]hept-2-ene-2-carboxylate

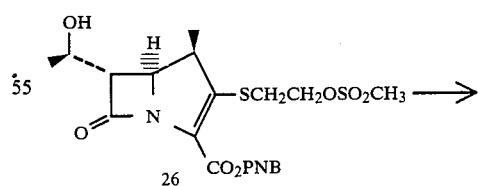

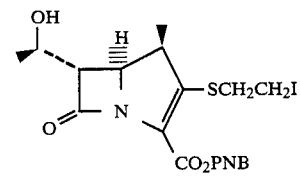

A solution of 367 mg (0.72 mmole) of intermediate 26 and 216 mg (1.4 mmole) of sodium iodide in 20 mL of acetone is heated at reflux for 4 hours. Evaporation of the acetone leaves a white amorphous solid which is suspended in ether (10 mL), water (10 mL). Filtration of the white solid and vacuum drying gives the title compound 27.

D.
3-[2-(1-Tetrahydrothiophenium)ethylthio]-6α-[1-(R)-hydroxyethyl]-4β-methyl-7-oxo-1-azabicyclo[3.2.0-]hept-2-ene-2-carboxylate

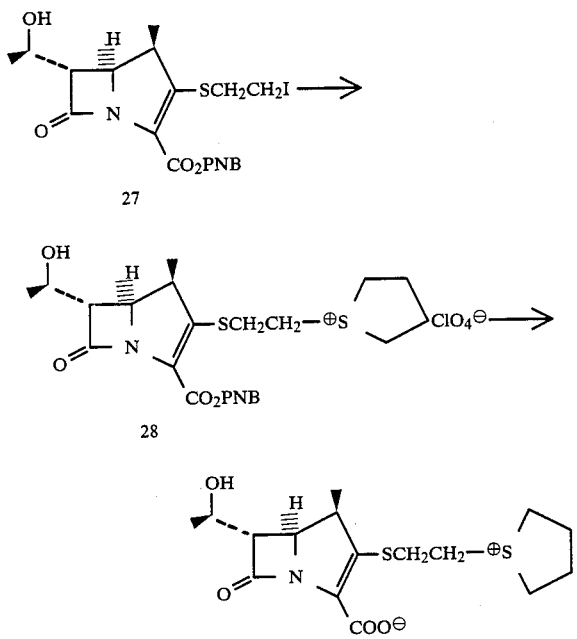

Tetrahydrothiphene (0.03 mL; 0.35 mmole) is added to a solution of p-nitrobenzyl 3-(2-iodoethylthio)-6α-[1-(R)-hydroxyethyl]-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 1 h, the solvent is removed to leave crude 28. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 20

Preparation of 3-[2-[4-(1,4-Oxathianium)]ethylthio]-6α-[1-(R)-hydroxyethyl]-4β-methyl-7-oxo-1-azabicyclo[3.2.0]hept-2-ene-2-carboxylate

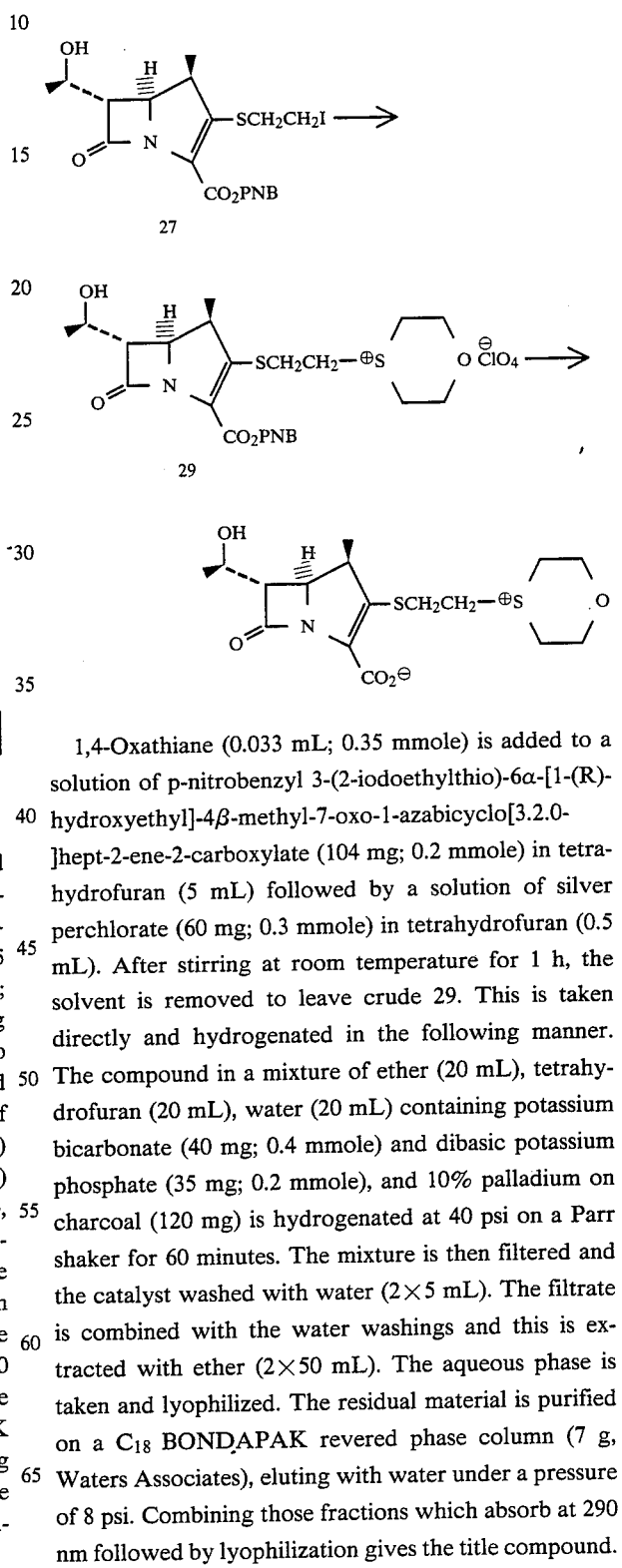

1,4-Oxathiane (0.033 mL; 0.35 mmole) is added to a solution of p-nitrobenzyl 3-(2-iodoethylthio)-6α-[1-(R)-hydroxyethyl]-4β-methyl-7-oxo-1-azabicyclo[3.2.0-]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 1 h, the solvent is removed to leave crude 29. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK revered phase column (7 g, Waters Associates), eluting with water under a pressure of 8 psi. Combining those fractions which absorb at 290 nm followed by lyophilization gives the title compound.

EXAMPLE 21

Preparation of 3-[2-[p-Chlorophenyl(methyl)sulfonium]ethylthio]-6α-[1-(R)-hydroxyethyl]-4β-methyl-7-oxo-1-azabicyclo[3.2.0]hept-2-ene-2-carboxylate

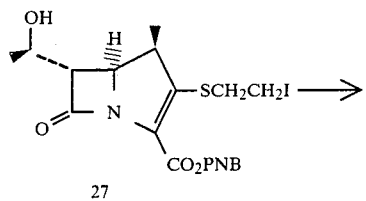
27

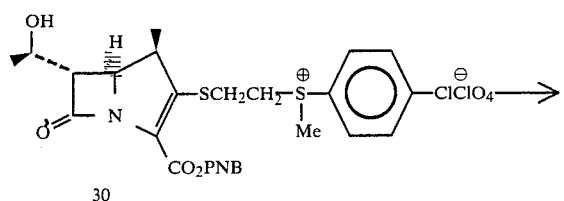
30

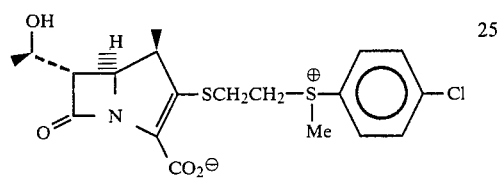

p-Chlorothioanisole (56 mg; 0.35 mmole) is added to a solution of p-nitrobenzyl 3-(2-iodoethylthio)-6α-[1-(R)-hydroxyethyl]-4β-methyl-7-oxo-1-azabicyclo[3.2.0]hept-2-ene-2-carboxylate (104 mg; 0.2 mmole) in tetrahydrofuran (5 mL) followed by a solution of silver perchlorate (60 mg; 0.3 mmole) in tetrahydrofuran (0.5 mL). After stirring at room temperature for 2 h, the solvent is removed to leave crude 30. This is taken directly and hydrogenated in the following manner. The compound in a mixture of ether (20 mL), tetrahydrofuran (20 mL), water (20 mL) containing potassium bicarbonate (40 mg; 0.4 mmole) and dibasic potassium phosphate (35 mg; 0.2 mmole), and 10% palladium on charcoal (120 mg) is hydrogenated at 40 psi on a Parr shaker for 60 minutes. The mixture is then filtered and the catalyst washed with water (2×5 mL). The filtrate is combined with the water washings and this is extracted with ether (2×50 mL). The aqueous phase is taken and lyophilized. The residual material is purified on a $C_{18}$ BONDAPAK reversed phase column (7 g, Waters Associates), eluting with water under a pressure of 8 psi. Combining those fractions which absorb at 290 nm followed by lyophilization gives the title compound.

EXAMPLE 22

Following the foregoing examples and text, the following compounds may be prepared by use of the appropriate sulfide.

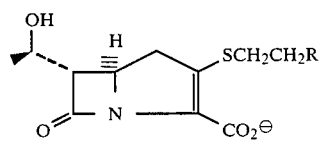

R

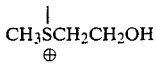

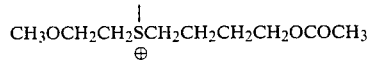

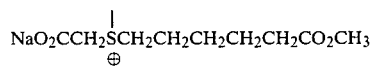

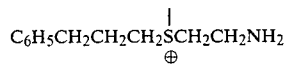

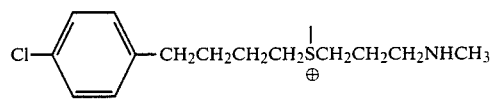

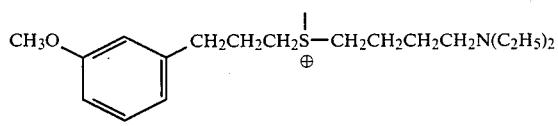

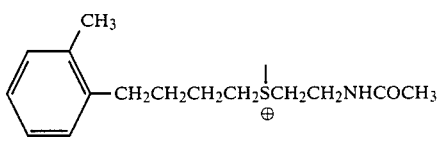

-continued
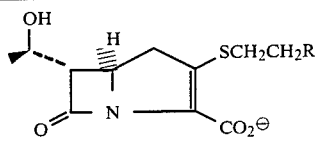
R
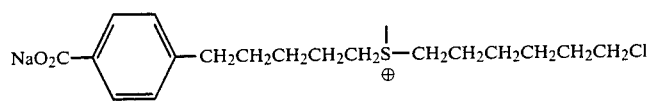
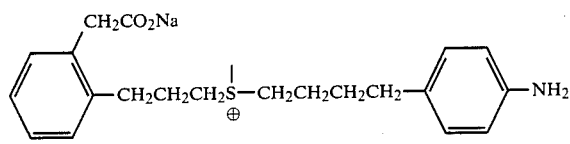
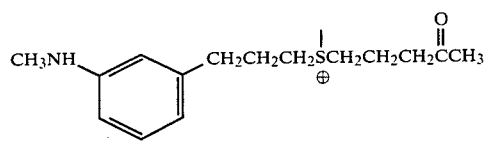
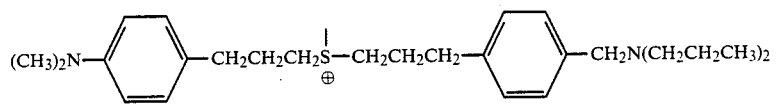
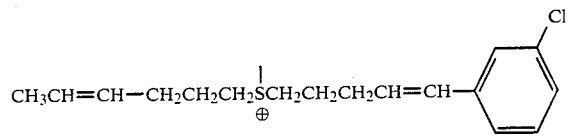
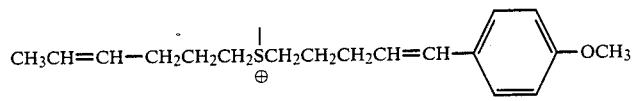
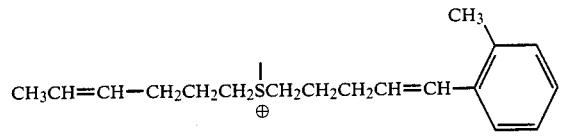
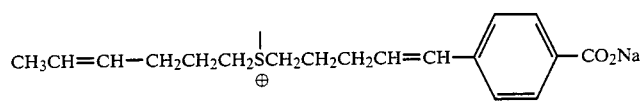
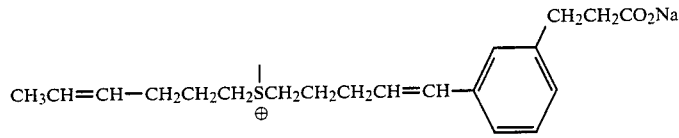

-continued
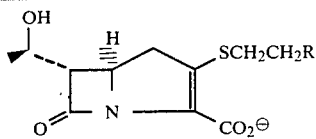
R
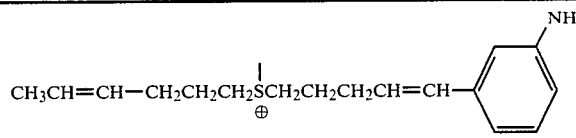
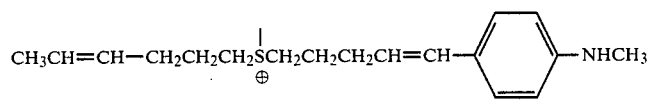
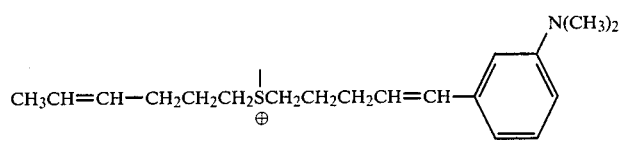
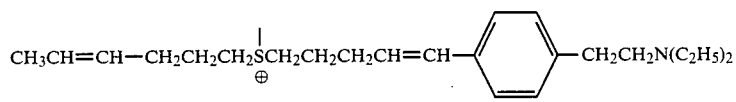
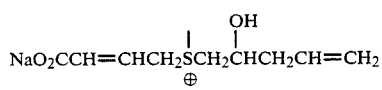 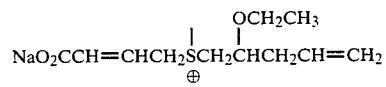
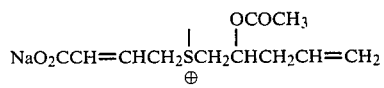 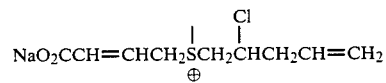
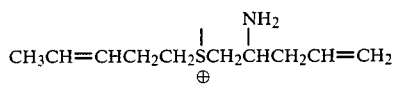 
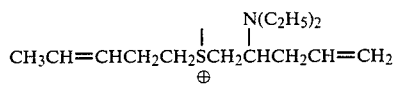 
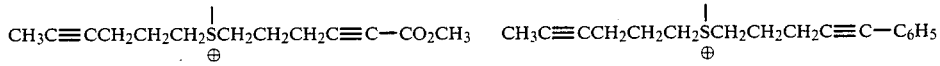
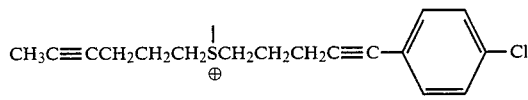
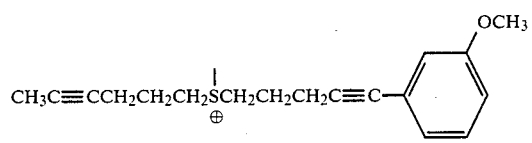
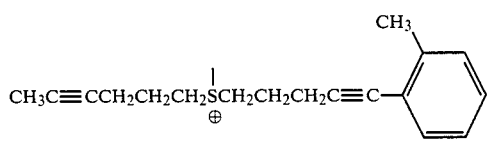

-continued
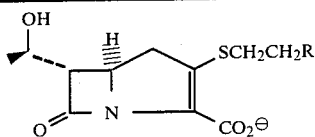
| R |
|---|
| 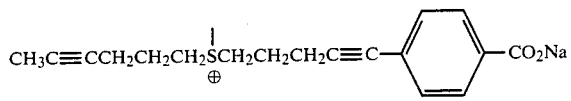 |
| 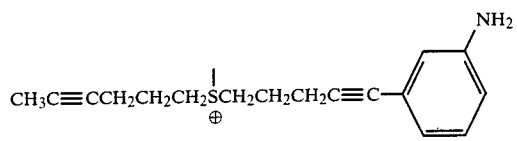 |
| 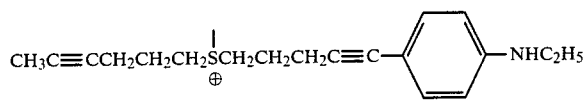 |
| 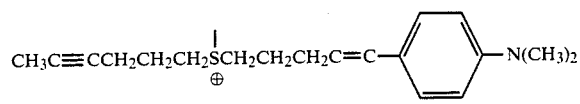 |
| 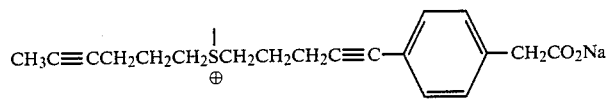 |
| 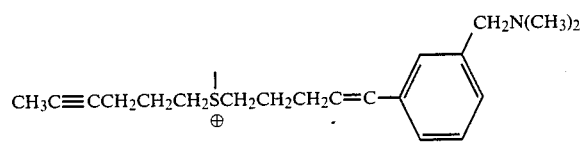 |
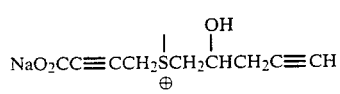 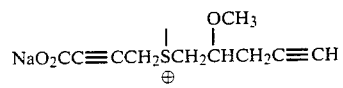
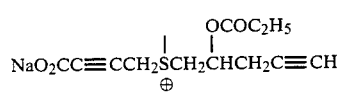 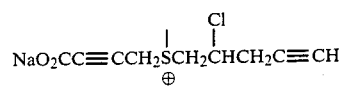
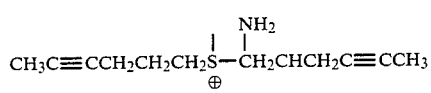 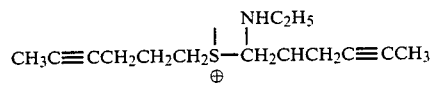
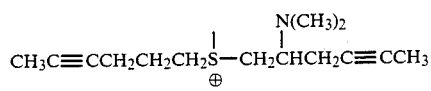 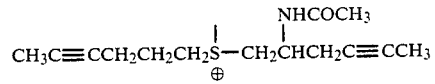
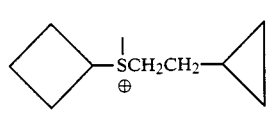 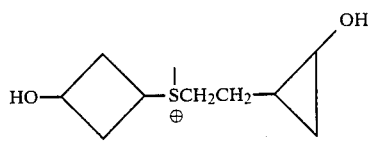
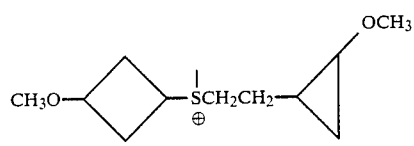 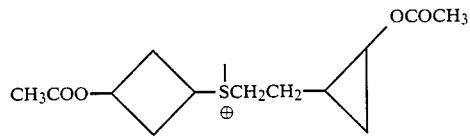

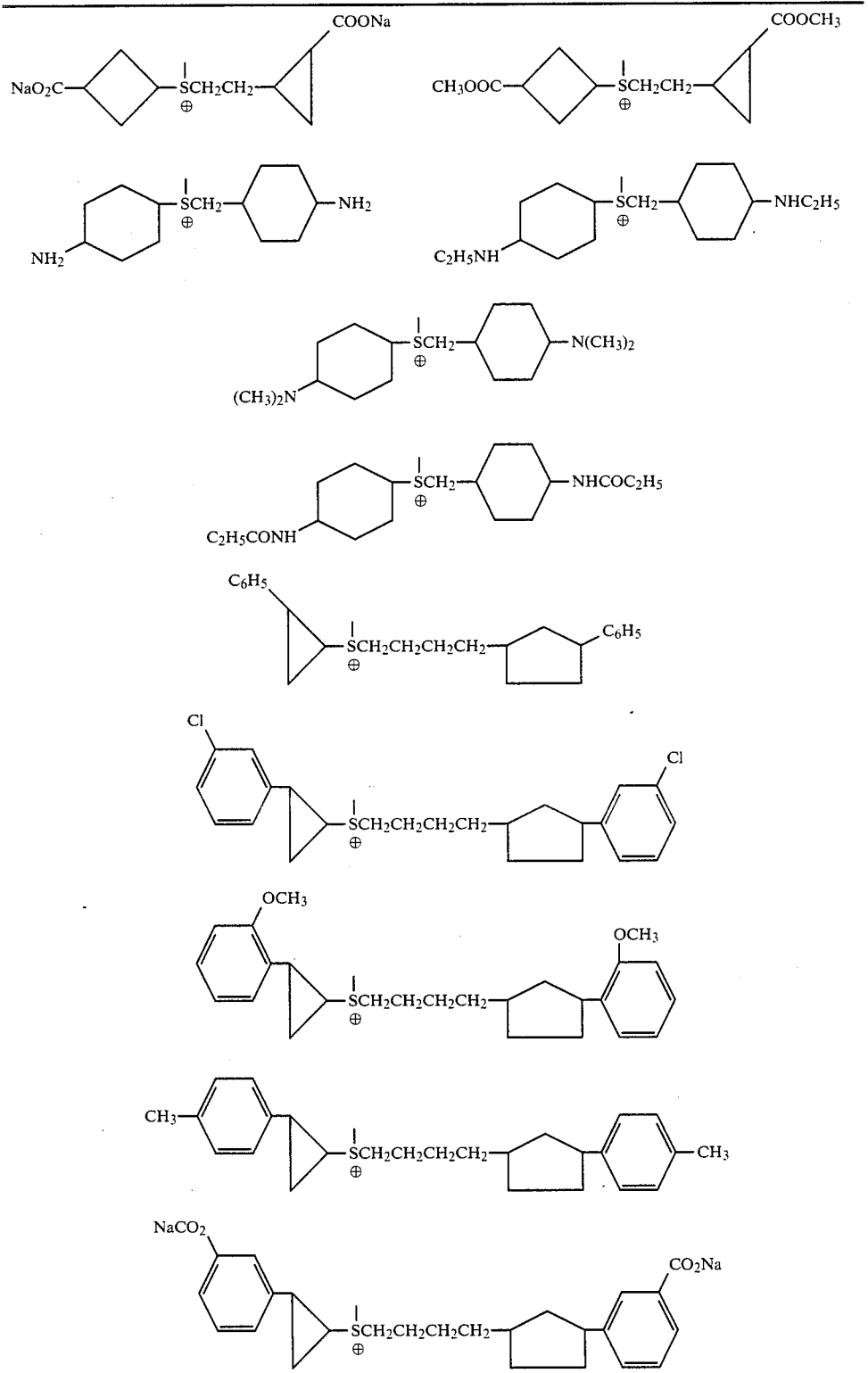

-continued
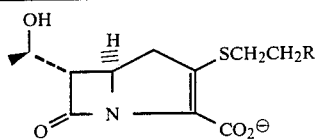
| R |
|---|
| 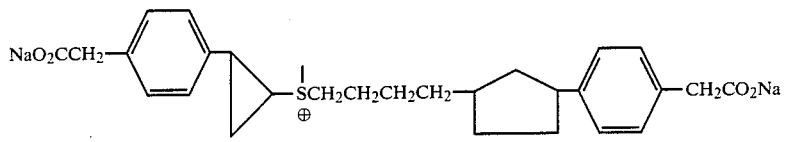 |
| 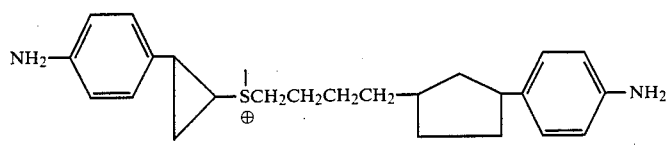 |
| 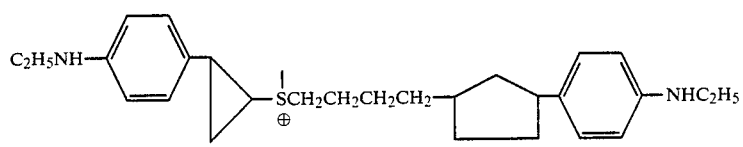 |
| 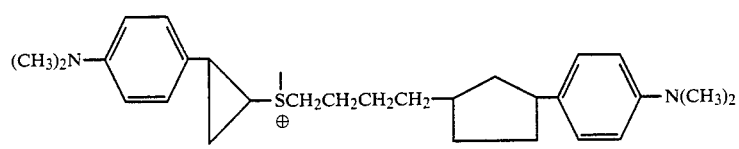 |
| 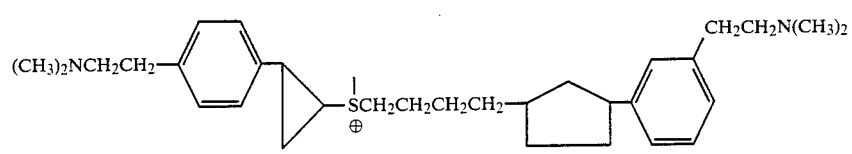 |
| 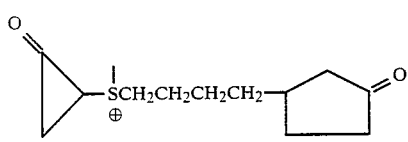 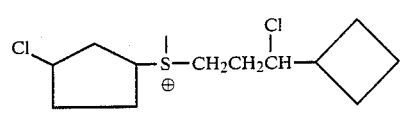 |
| 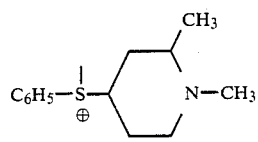 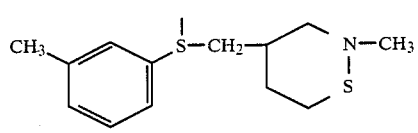 |
| 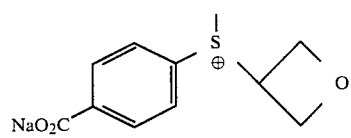 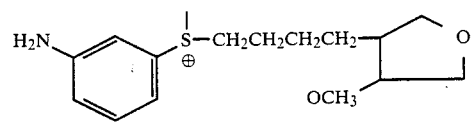 |
| 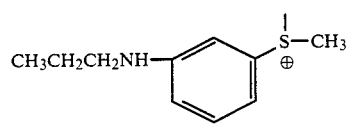 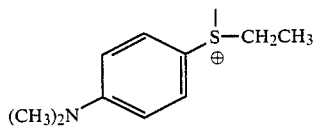 |

-continued
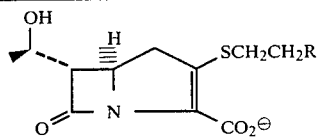
R
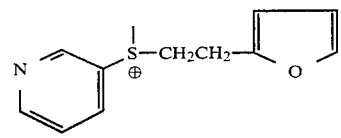 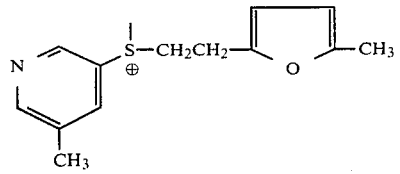
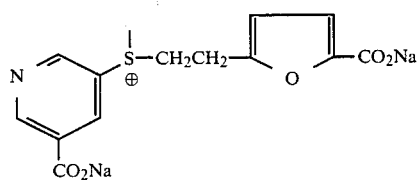 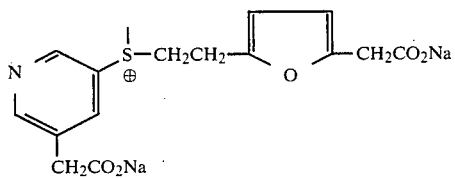
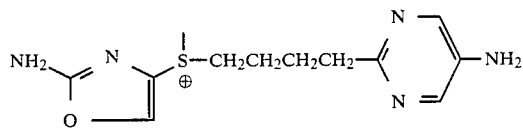
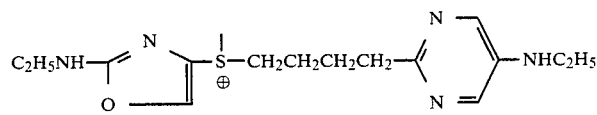
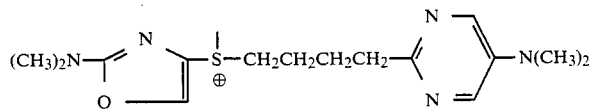
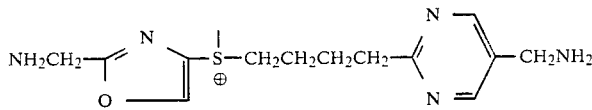
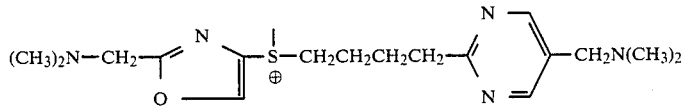
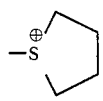 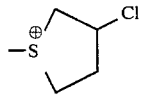
 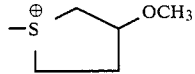
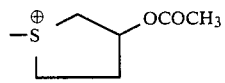 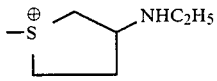
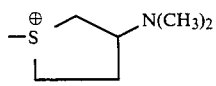 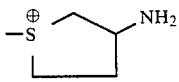

-continued
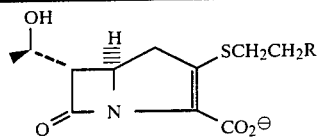
| R | |
|---|---|
| 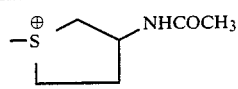 | 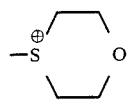 |
| 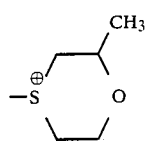 | 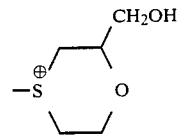 |
| 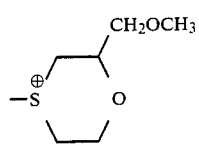 | 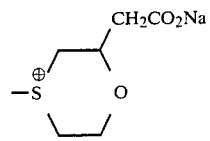 |
| 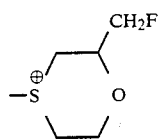 | 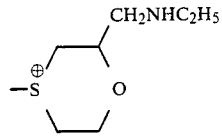 |
| 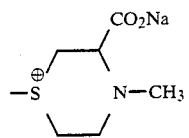 | 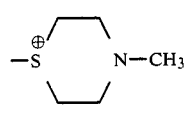 |
| 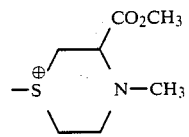 | 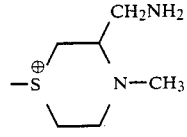 |
| 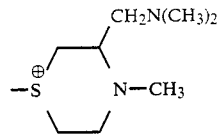 | 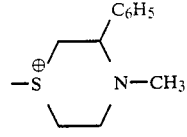 |
| 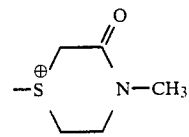 | 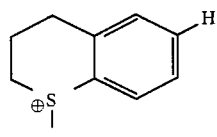 |
| 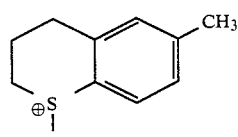 | 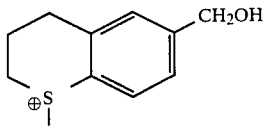 |
| 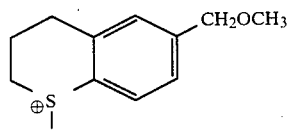 | 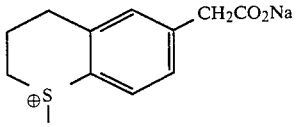 |

-continued
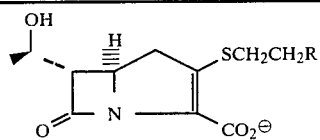
R
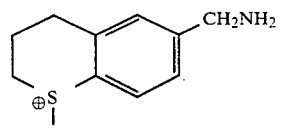 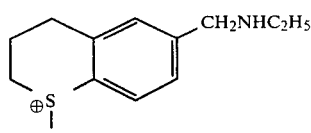
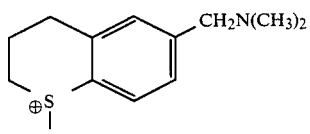 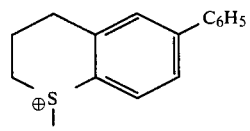
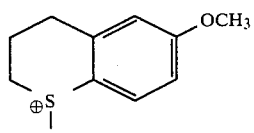 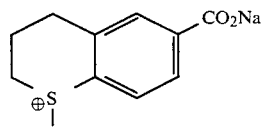
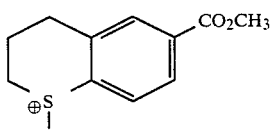 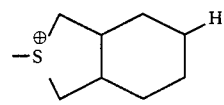
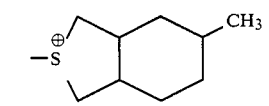 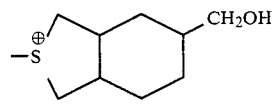
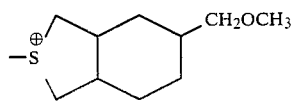 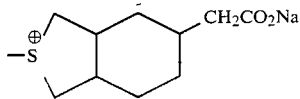
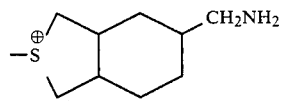 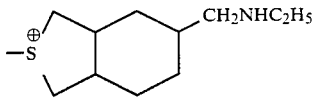
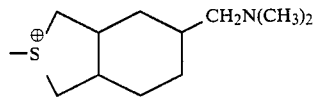 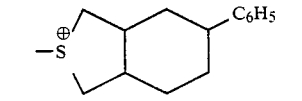
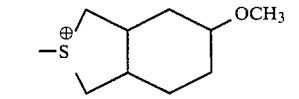 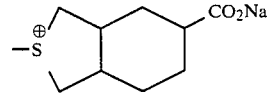
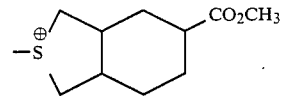 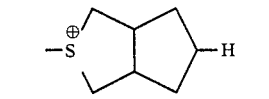
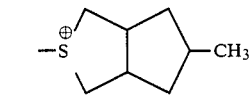 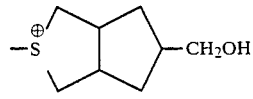

-continued
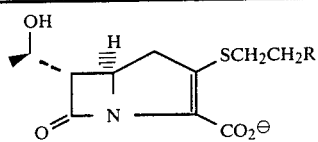
R
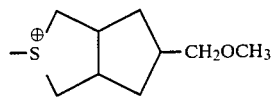 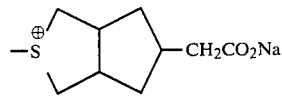
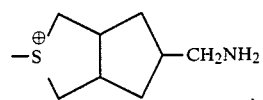 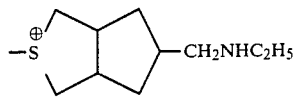
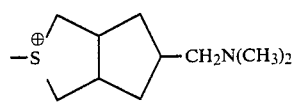 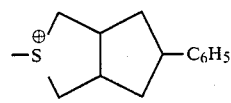
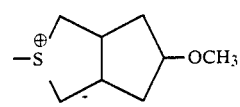 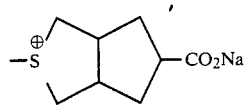
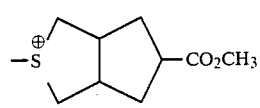 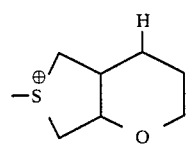
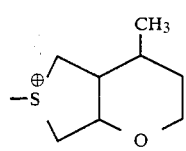 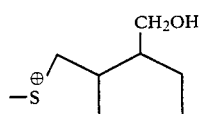
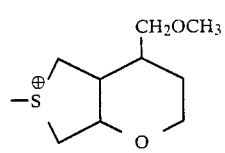 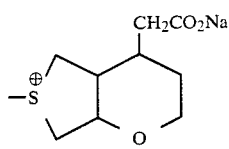
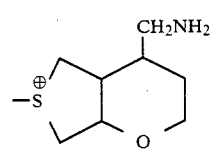 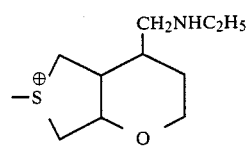
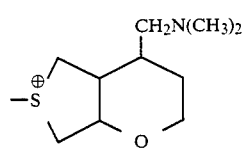 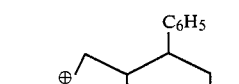
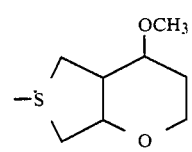 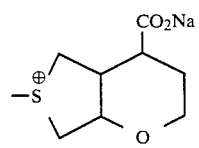

-continued
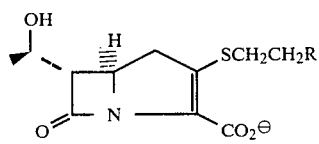
R
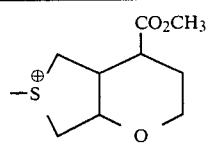 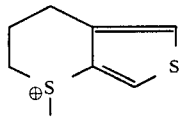
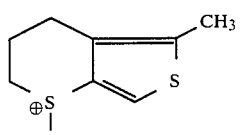 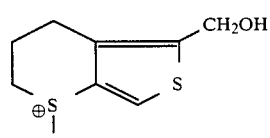
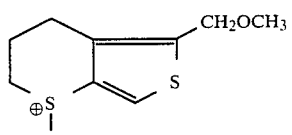 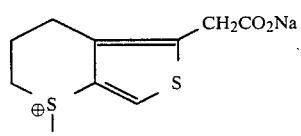
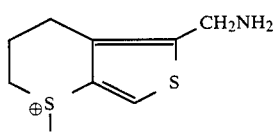 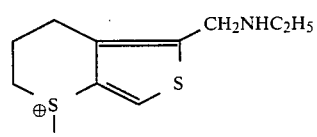
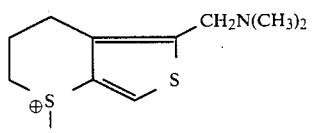 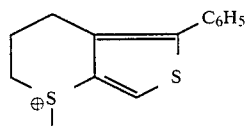
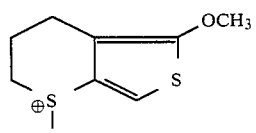 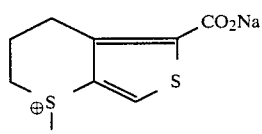
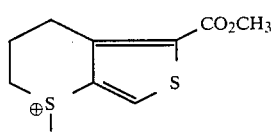 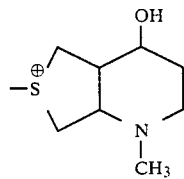
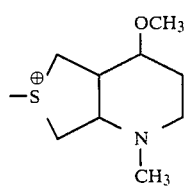 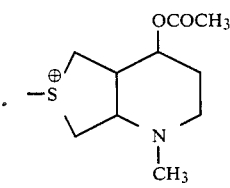

| | |
|---|---|
| 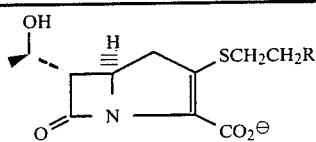 | |
| R | |
| 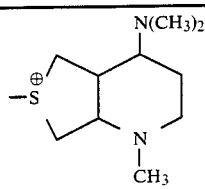 | 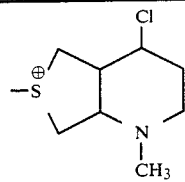 |
| 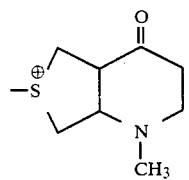 | 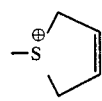 |
| 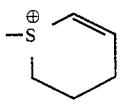 | 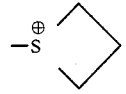 |
EXAMPLE 23
Following the foregoing Examples and text, the following compounds may be prepared by use of the appropriate sulfide.
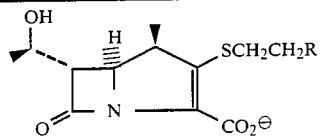
| | |
|---|---|
| 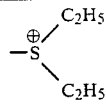 | 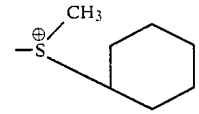 |
| 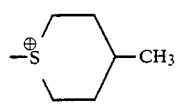 | 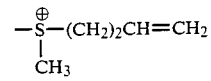 |
| 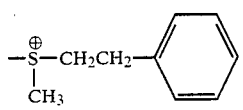 | 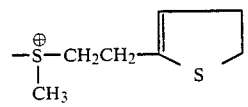 |
| 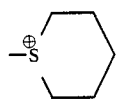 | 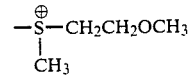 |
| 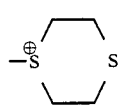 | 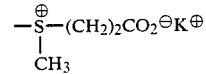 |

-continued
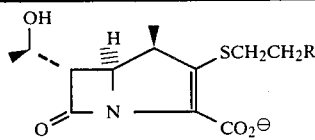
| R | |
|---|---|
| 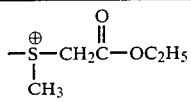 | 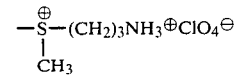 |
| 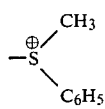 | 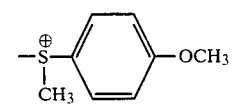 |
| 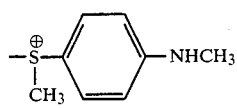 |  |
| 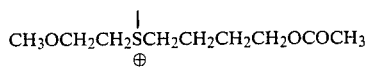 | 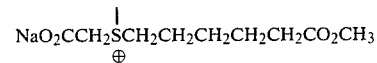 |
| 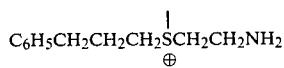 | 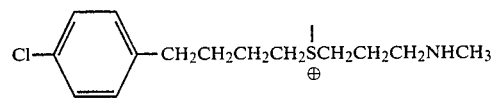 |
| 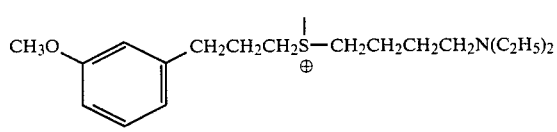 | 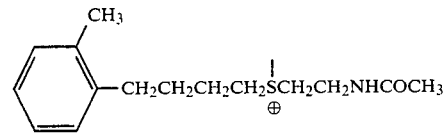 |
| 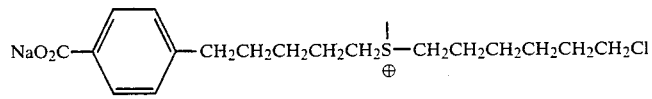 | |
| 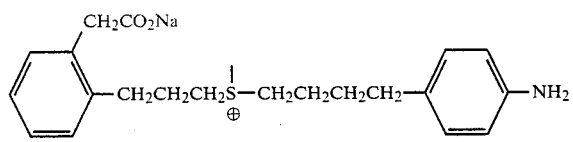 | 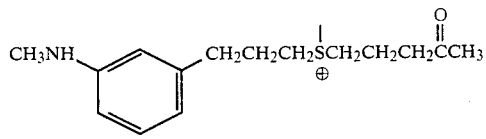 |
| 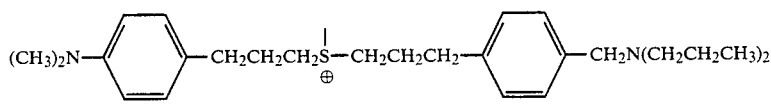 | |
| 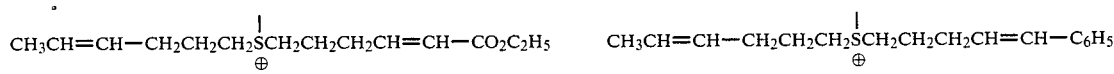 |  |
| 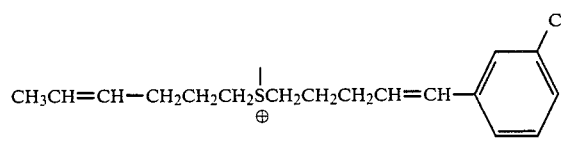 | |
| 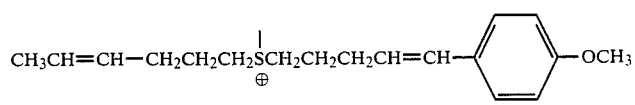 | |

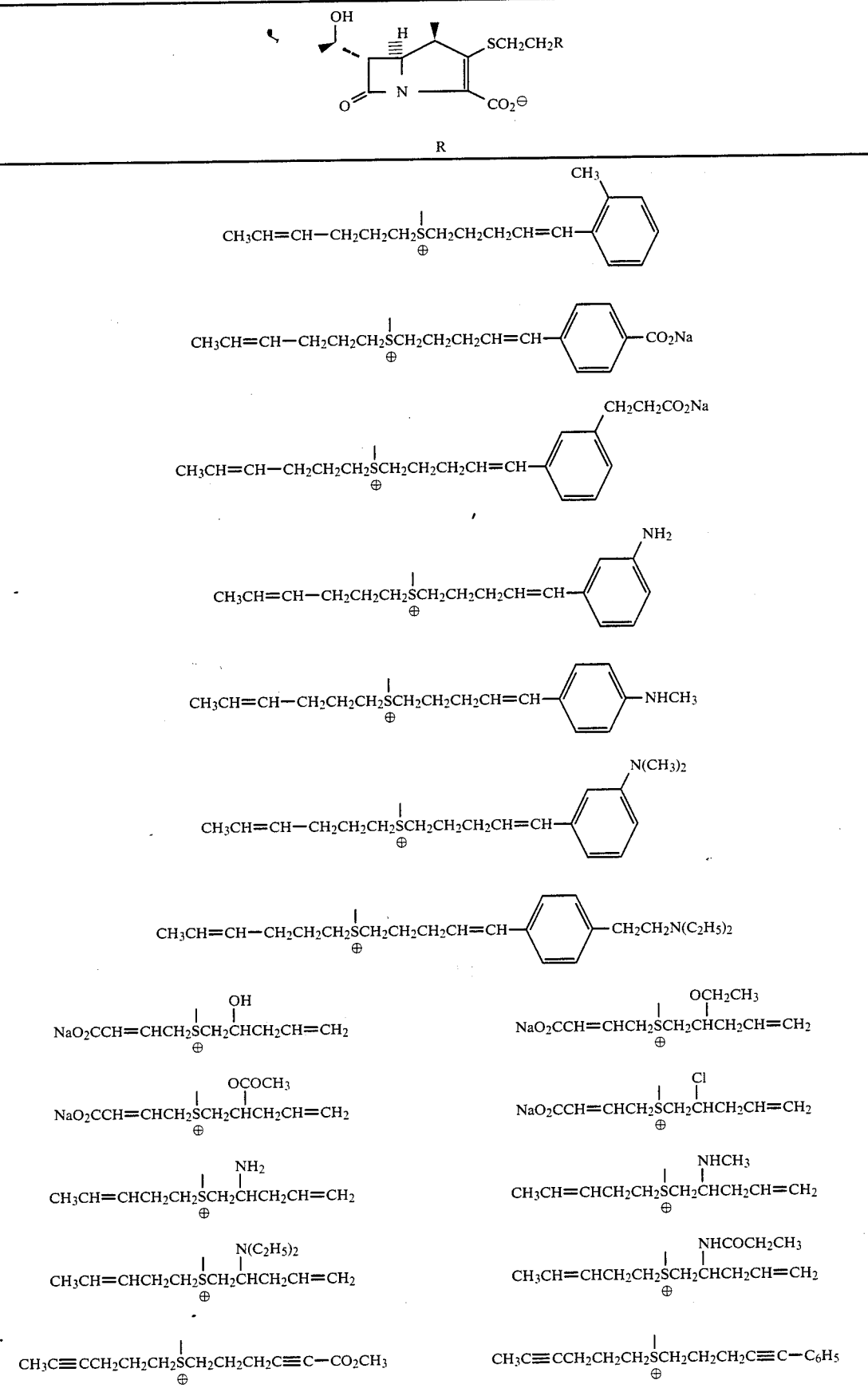

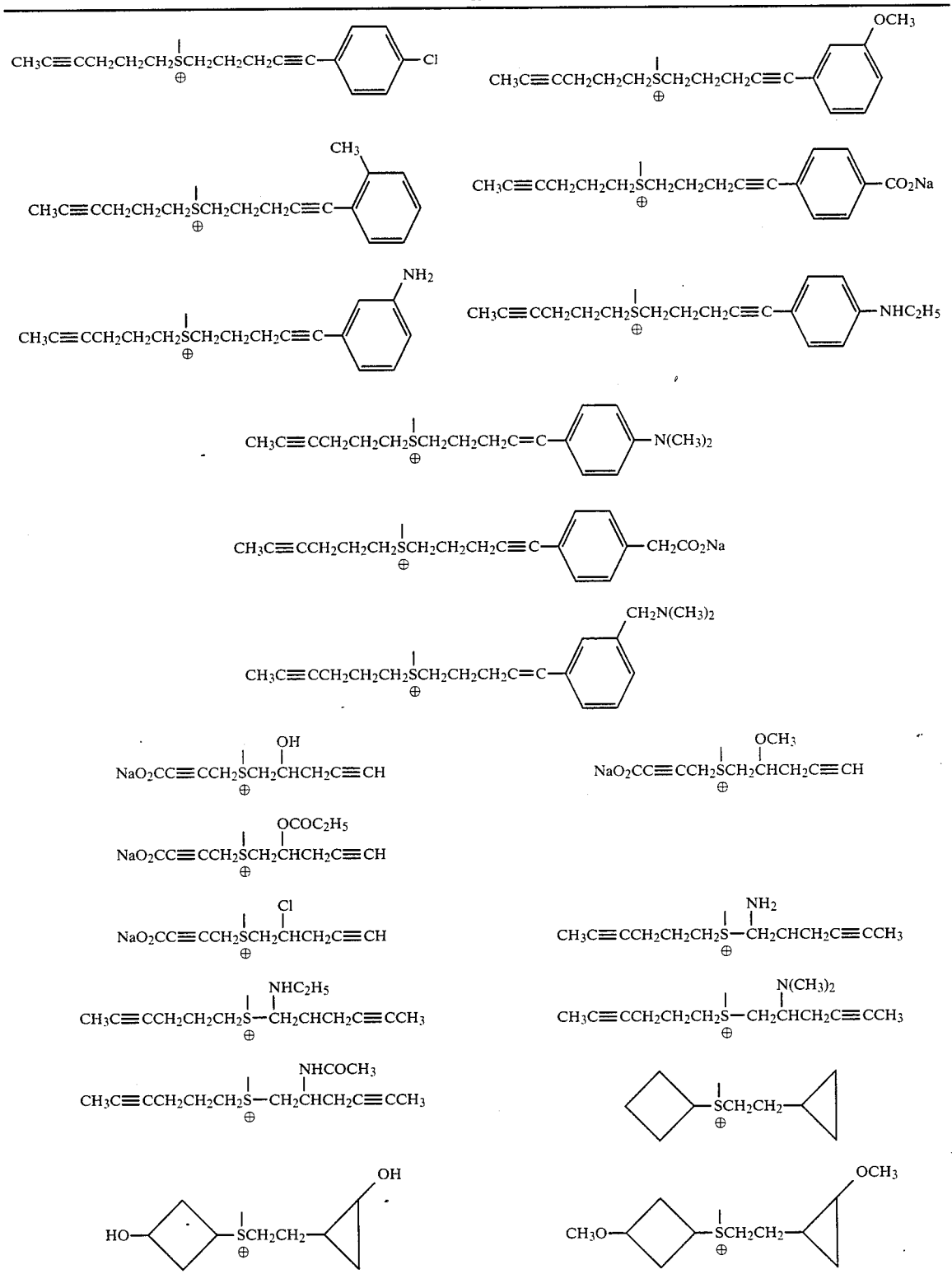

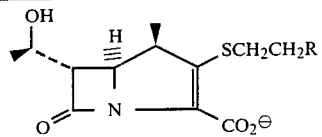
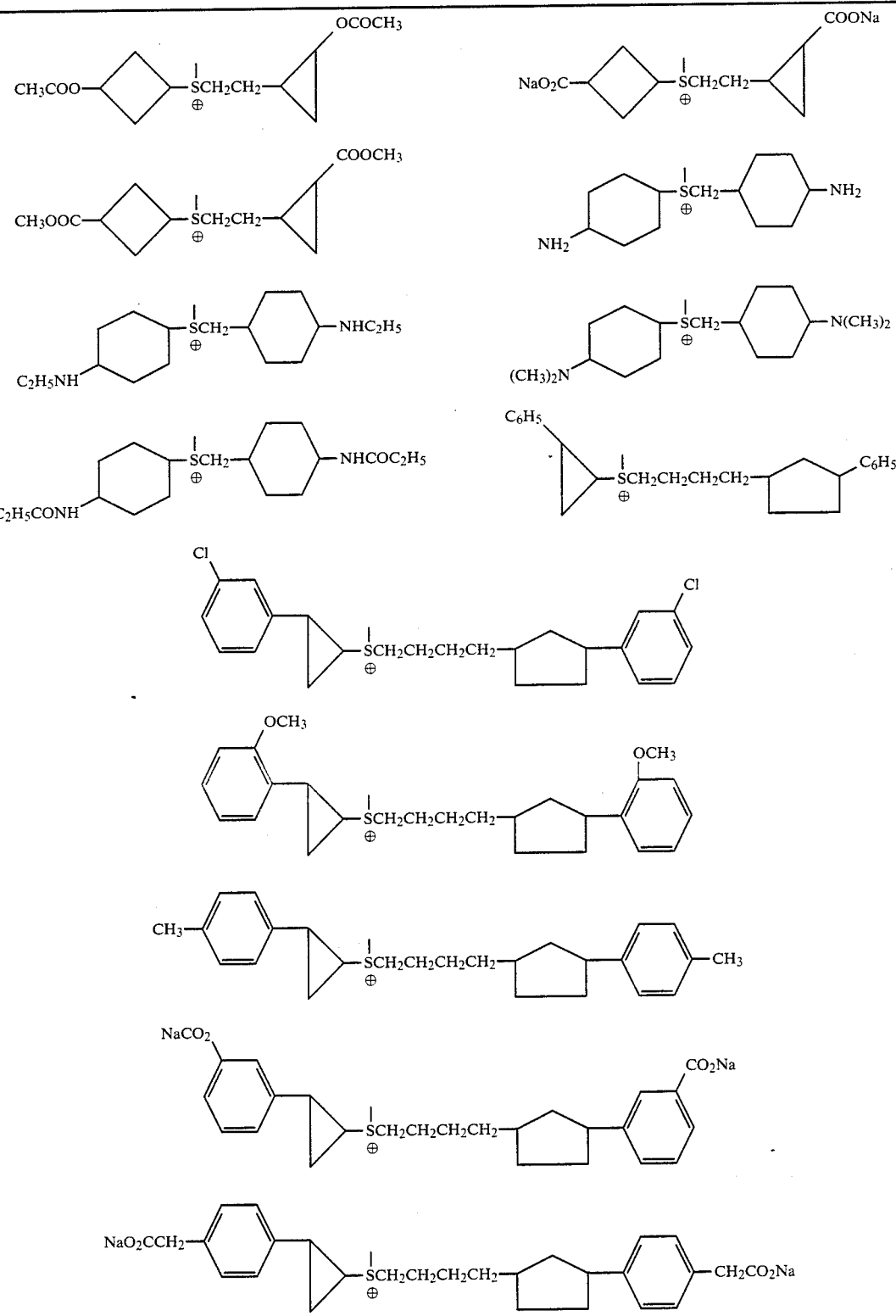

-continued
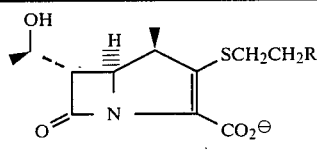
R
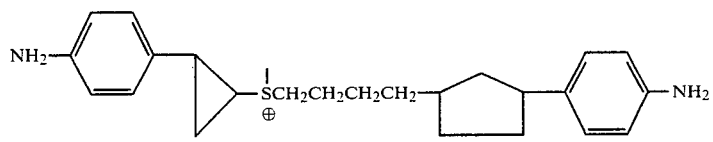
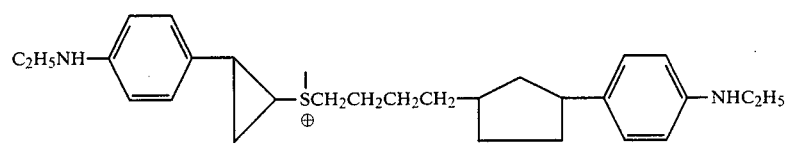
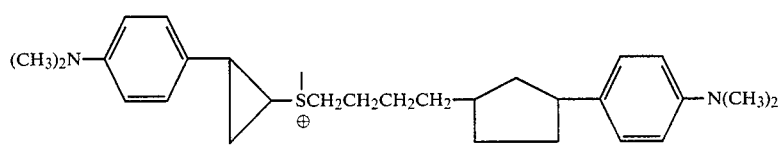
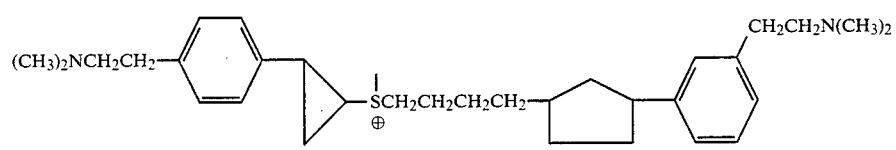
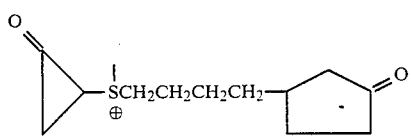
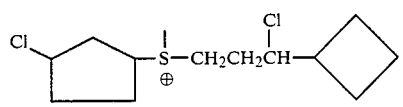
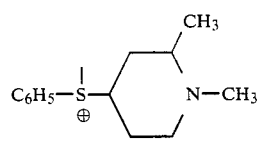
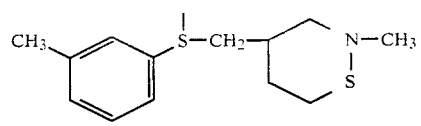
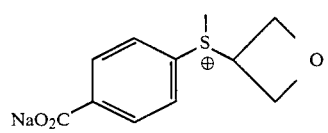
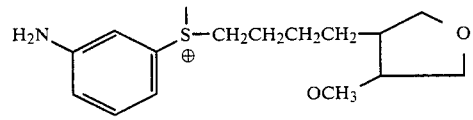
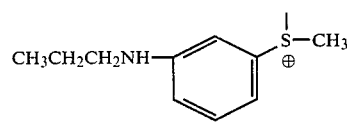
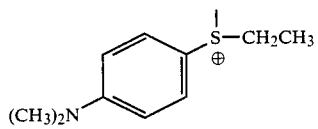
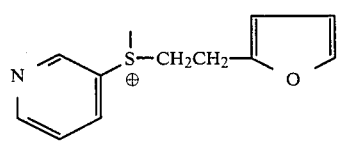
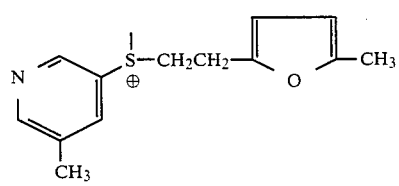

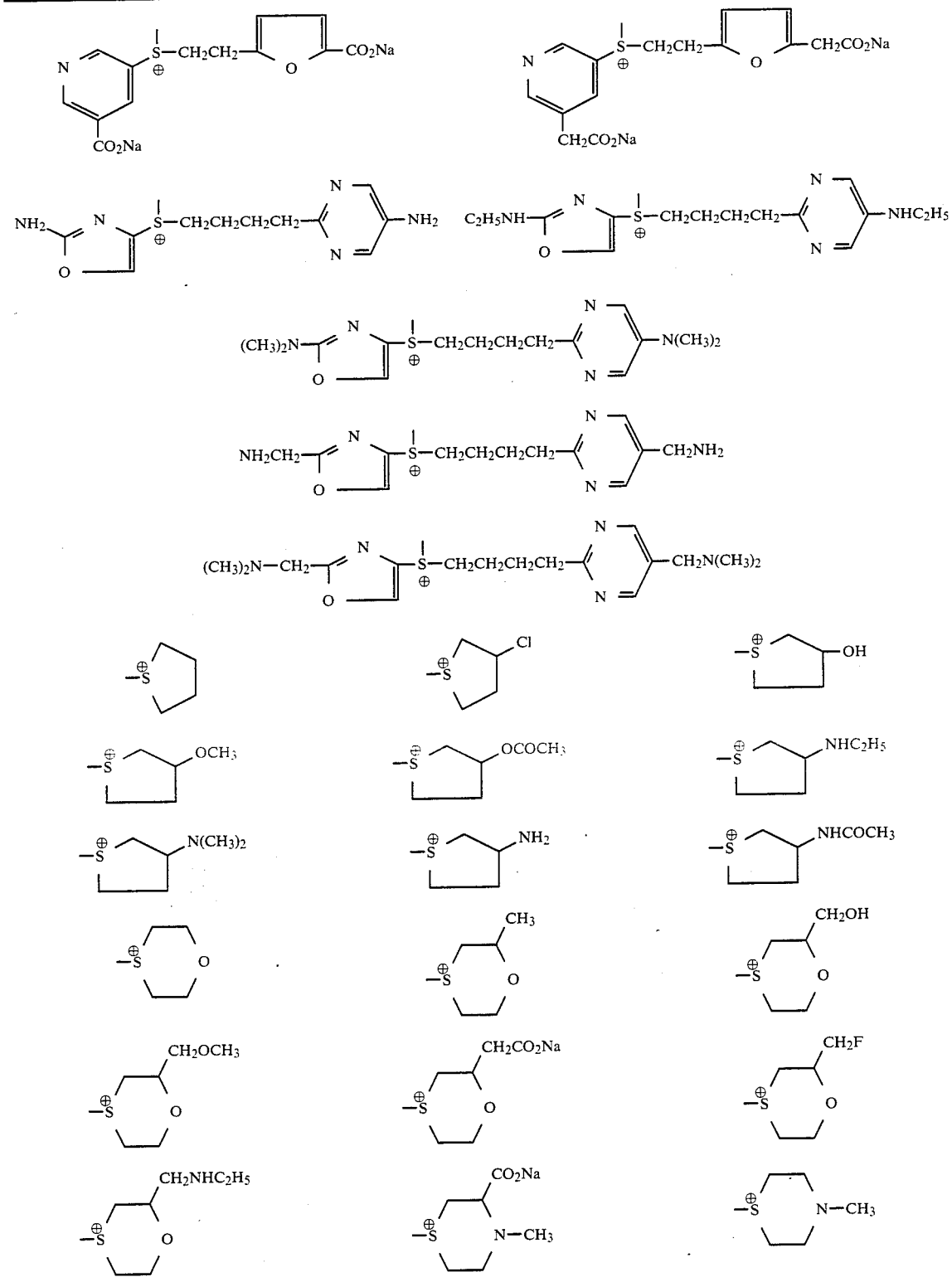

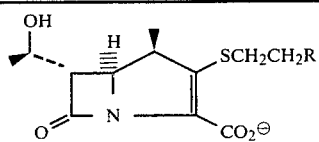

-continued

[Chemical structure: carbapenem core with OH, H stereochemistry, SCH₂CH₂R substituent, and CO₂⁻ group]

| R | | |
|---|---|---|

-continued
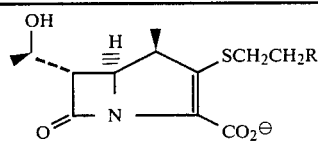
| R | | |
|---|---|---|
| 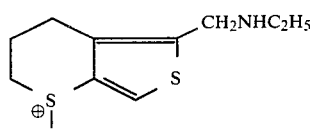 | 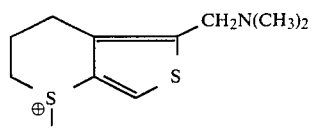 | 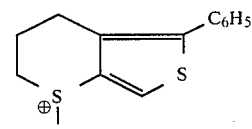 |
| 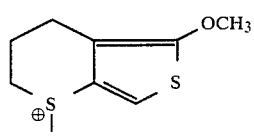 | 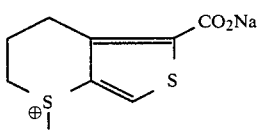 | 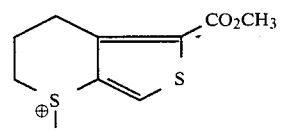 |
| 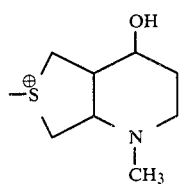 | 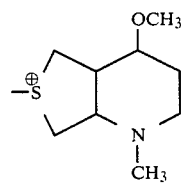 | 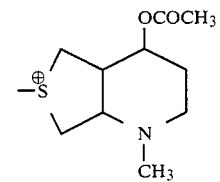 |
| 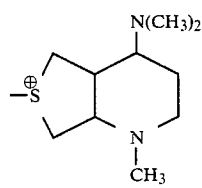 | 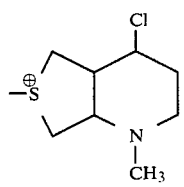 | 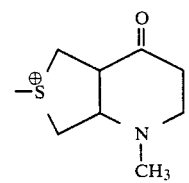 |
|  | 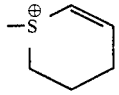 | 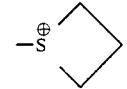 |
We claim:
1. A compound of the formula
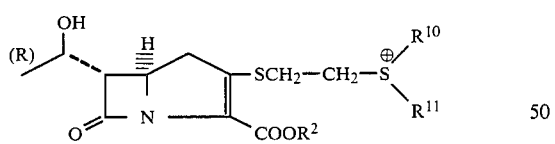
wherein $R^2$ is hydrogen, an anionic charge or a conventional readily removable carboxyl protecting group; and
$$-\overset{\oplus}{S}\diagdown_{R^{11}}^{R^{10}} \text{ represents}$$
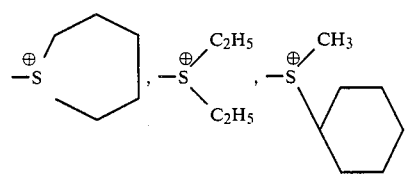
-continued
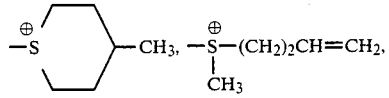
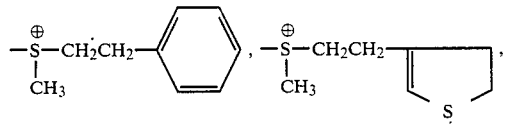
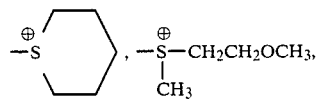
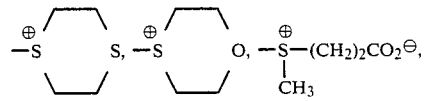

-continued

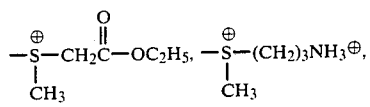

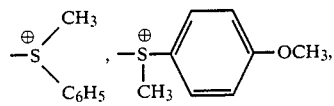

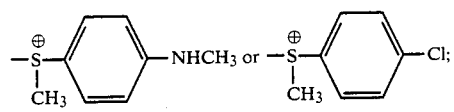

or a pharmaceutically acceptable salt thereof.

2. A compound of the formula

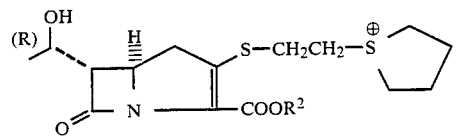

wherein $R^2$ is hydrogen, an anionic charge or a conventional readily removable carboxyl protecting group, providing that when $R^2$ is hydrogen or a protecting group, there is also present a counter anion, or a pharmaceutically acceptable salt thereof.

3. The compound according to claim 2 wherein $R^2$ is p-nitrobenzyl or allyl.

4. The compound according to claim 2 wherein $R^2$ is an anionic charge.

5. A compound of the formula

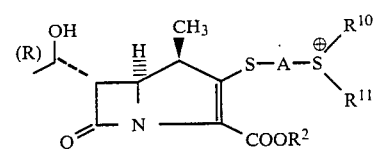

wherein $R^2$ is hydrogen, an anionic charge or a conventional readily removable carboxyl protecting group; and

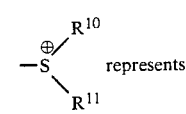 represents

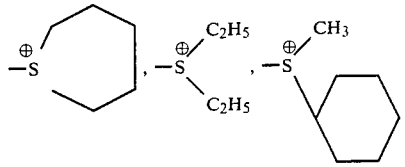

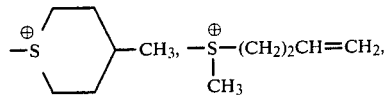

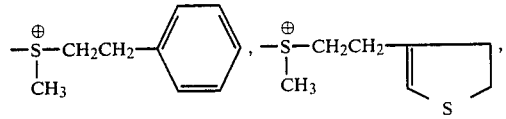

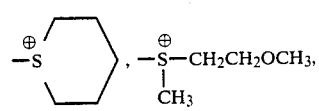

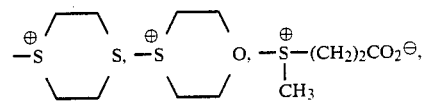

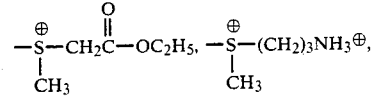

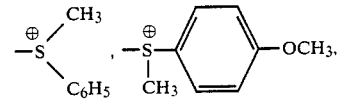

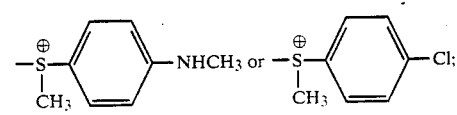

or a pharmaceutically acceptable salt thereof.

6. A compound of the formula

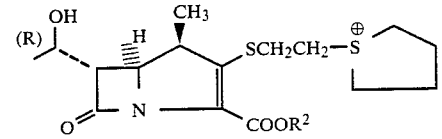

wherein $R^2$ is hydrogen, an anionic charge or a conventional readily removable carboxyl protecting group, providing that when $R^2$ is hydrogen or a protecting group, there is also present a counter anion, or a pharmaceutically acceptable salt thereof.

7. The compound according to claim 6 wherein $R^2$ is p-nitrobenzyl or allyl.

8. The compound according to claim 6 wherein $R^2$ is an anionic charge.

* * * * *